US010520832B2

(12) United States Patent
Levinski et al.

(10) Patent No.: US 10,520,832 B2
(45) Date of Patent: Dec. 31, 2019

(54) TOPOGRAPHIC PHASE CONTROL FOR OVERLAY MEASUREMENT

(71) Applicant: KLA-Tencor Corporation, Milpitas, CA (US)

(72) Inventors: Vladimir Levinski, Migdal HaEmek (IL); Yuri Paskover, Caesarea (IL); Amnon Manassen, Haifa (IL); Yoni Shalibo, Binyamina (IL)

(73) Assignee: KLA-Tencor Corporation, Milpitas, CA (US)

( * ) Notice: Subject to any disclaimer, the term of this patent is extended or adjusted under 35 U.S.C. 154(b) by 132 days.

(21) Appl. No.: 15/114,175

(22) PCT Filed: May 19, 2016

(86) PCT No.: PCT/US2016/033353
§ 371 (c)(1),
(2) Date: Jul. 26, 2016

(87) PCT Pub. No.: WO2016/187468
PCT Pub. Date: Nov. 24, 2016

(65) Prior Publication Data
US 2017/0146915 A1 May 25, 2017

Related U.S. Application Data

(60) Provisional application No. 62/163,783, filed on May 19, 2015, provisional application No. 62/222,724, filed on Sep. 23, 2015.

(51) Int. Cl.
G03F 7/20 (2006.01)
G02B 7/38 (2006.01)
(Continued)

(52) U.S. Cl.
CPC .......... *G03F 7/70633* (2013.01); *G02B 7/38* (2013.01); *G02B 27/32* (2013.01); *G06T 7/80* (2017.01); *H04N 5/23212* (2013.01)

(58) Field of Classification Search
None
See application file for complete search history.

(56) References Cited

U.S. PATENT DOCUMENTS 7,230,704 B2  6/2007 Sezginer et al.
7,433,040 B2  10/2008 Mieher et al.
(Continued)

FOREIGN PATENT DOCUMENTS

WO  2007143056  12/2007
WO  2016086056  6/2016

OTHER PUBLICATIONS

Creath, Calibration of numerical aperture effects in interferometric microscope objectives, 1989.*
(Continued)

*Primary Examiner* — Michael J Hess
(74) *Attorney, Agent, or Firm* — Hodgson Russ LLP

(57) ABSTRACT

Metrology tools and methods are provided, which estimate the effect of topographic phases corresponding to different diffraction orders, which result from light scattering on periodic targets, and adjust the measurement conditions to improve measurement accuracy. In imaging, overlay error magnification may be reduced by choosing appropriate measurement conditions based on analysis of contrast function behavior, changing illumination conditions (reducing spectrum width and illumination NA), using polarizing targets and/or optical systems, using multiple defocusing positions etc. On-the-fly calibration of measurement results may be carried out in imaging or scatterometry using additional measurements or additional target cells.

7 Claims, 15 Drawing Sheets

(51) Int. Cl.
*G06T 7/80* (2017.01)
*G02B 27/32* (2006.01)
*H04N 5/232* (2006.01)

(56) References Cited

U.S. PATENT DOCUMENTS

| | | | |
|---|---|---|---|
| 8,582,114 B2 | 11/2013 | Manassen et al. | |
| 8,786,825 B2 | 7/2014 | Van De Kerkhof et al. | |
| 8,896,832 B2 | 11/2014 | Hill et al. | |
| 8,908,147 B2 | 12/2014 | Den Boef et al. | |
| 2004/0233440 A1 | 11/2004 | Mieher et al. | |
| 2004/0235205 A1* | 11/2004 | Levy | G01N 21/211 |
| | | | 438/14 |
| 2006/0164649 A1 | 7/2006 | Rosengaus | |
| 2010/0092882 A1* | 4/2010 | Matsumoto | G03B 27/42 |
| | | | 430/30 |
| 2011/0027704 A1* | 2/2011 | Cramer | G03F 7/70641 |
| | | | 430/30 |
| 2014/0060148 A1 | 3/2014 | Amit et al. | |
| 2014/0111791 A1 | 4/2014 | Manassen et al. | |
| 2015/0043803 A1* | 2/2015 | Jeong | G06T 7/001 |
| | | | 382/149 |
| 2015/0204664 A1* | 7/2015 | Bringoltz | G03F 7/70683 |
| | | | 356/492 |
| 2016/0334715 A1* | 11/2016 | Smilde | G03F 7/70625 |
| 2017/0176871 A1* | 6/2017 | Van Buel | G03F 7/70683 |

OTHER PUBLICATIONS

ISA/KR, International Search Report for PCT/US2016/033353 dated Oct. 18, 2016.
Adel, et al., Diffraction order control in overlay metrology—a review of the roadmap options, Metrology, Inspection, and Process Control for Microlithography XXII, 2008, Proc. of SPIE vol. 6922, pp. 692202-1-692202-19.
2013 Advanced Lithography, Technical Summaries, Part of Proc. of SPIE vol. 8679, www.spie.org/alconf, Feb. 25-28, 2013.

* cited by examiner

*200*

210 — DERIVING A DEPENDENCY OF AN OVERLAY MAGNIFICATION ERROR ON A LEVEL OF DEFOCUSING

220 — OPERATING THE OPTICAL SYSTEM AT A NARROW SPECTRAL RANGE, Δλ≤10NM, AT A NARROW ILLUMINATION NUMERICAL APERTURE, NA≤0.1, AND AT A FOCUS POSITION THAT CORRESPONDS TO ZERO OVERLAY MAGNIFICATION ERROR ACCORDING TO THE DERIVED DEPENDENCY

230 — GRABBING METROLOGY TARGET IMAGES AT CORRESPONDING FOCUS POSITIONS

240 — GRABBING THE IMAGES SIMULTANEOUSLY

242 — POSITIONING BEAM SPLITTING ELEMENTS ALONG A DETECTION PATH OF THE METROLOGY TOOL

244 — PROVIDING THE FOCUS POSITIONS, HAVING DIFFERENT DETECTION PATH LENGTHS, BY THE BEAM SPLITTERS

246 — USING A RETICLE AT A FIELD PLANE OF THE METROLOGY TOOL AS A REFERENCE FOR THE TARGET IMAGES AT THE FOCUS LOCATIONS

250 — ESTIMATING AN INACCURACY MAGNIFICATION FACTOR OF THE GRABBED IMAGES

Figure 10

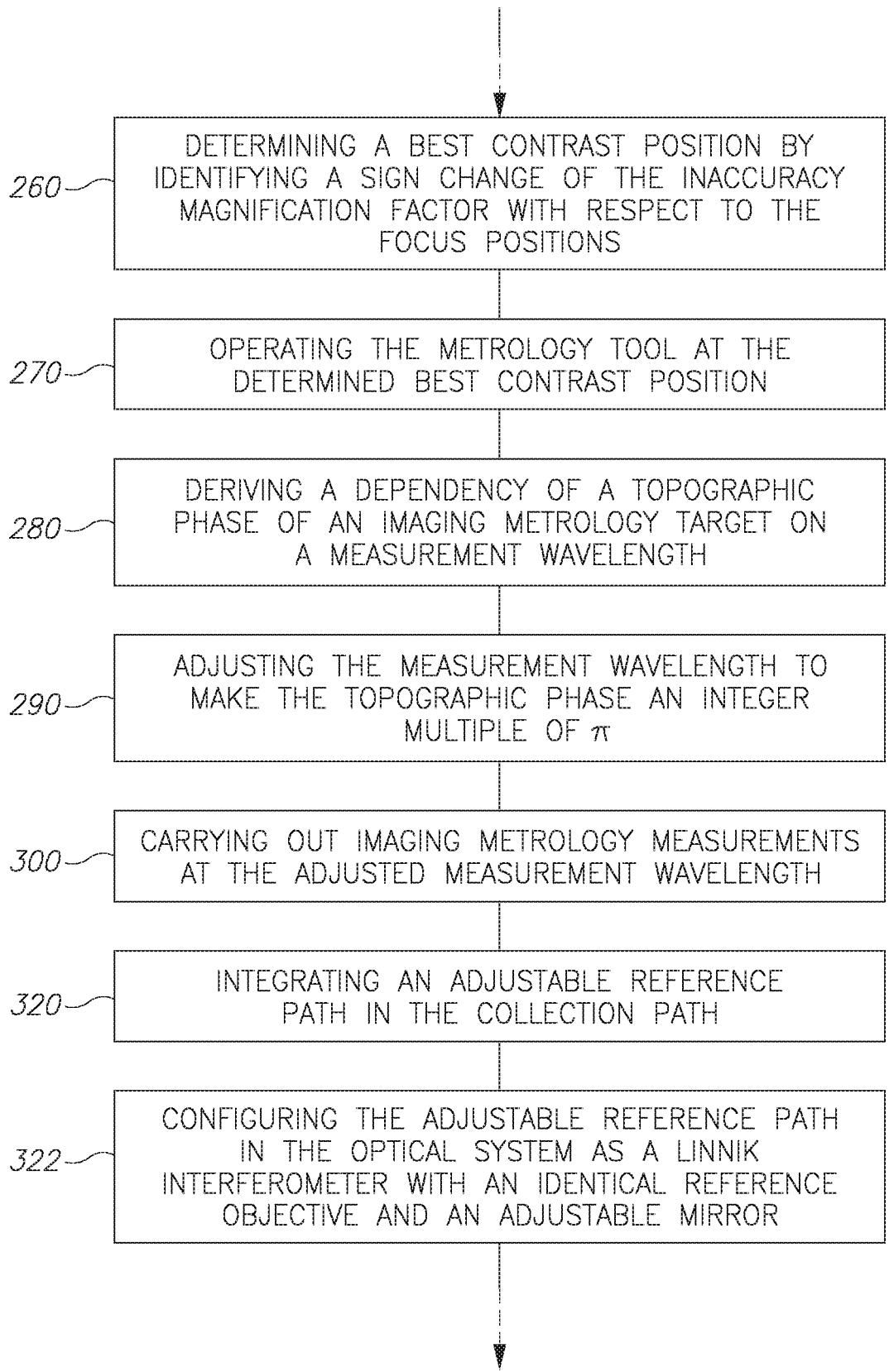
Figure 10 (cont. 1)

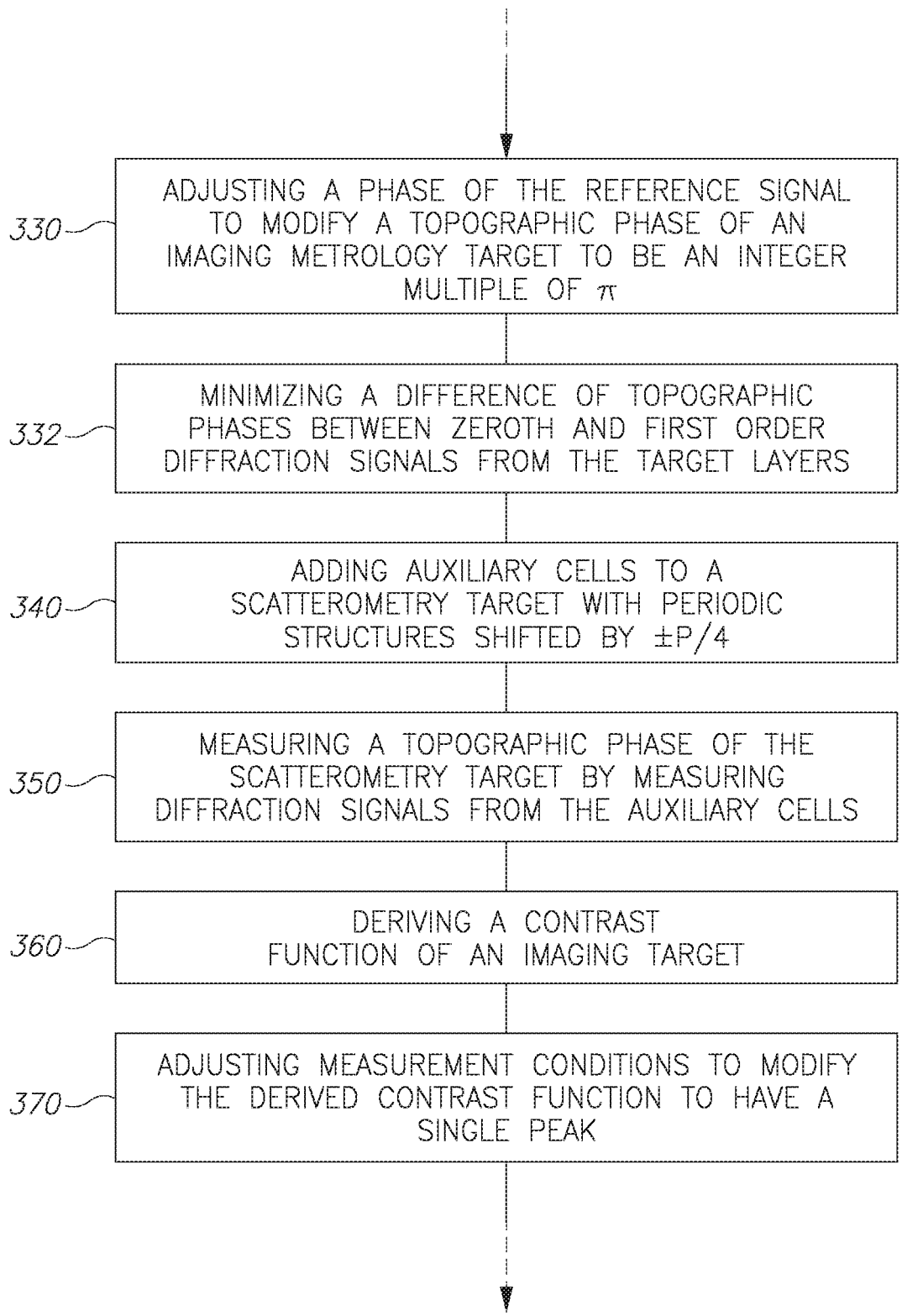
Figure 10 (cont. 2)

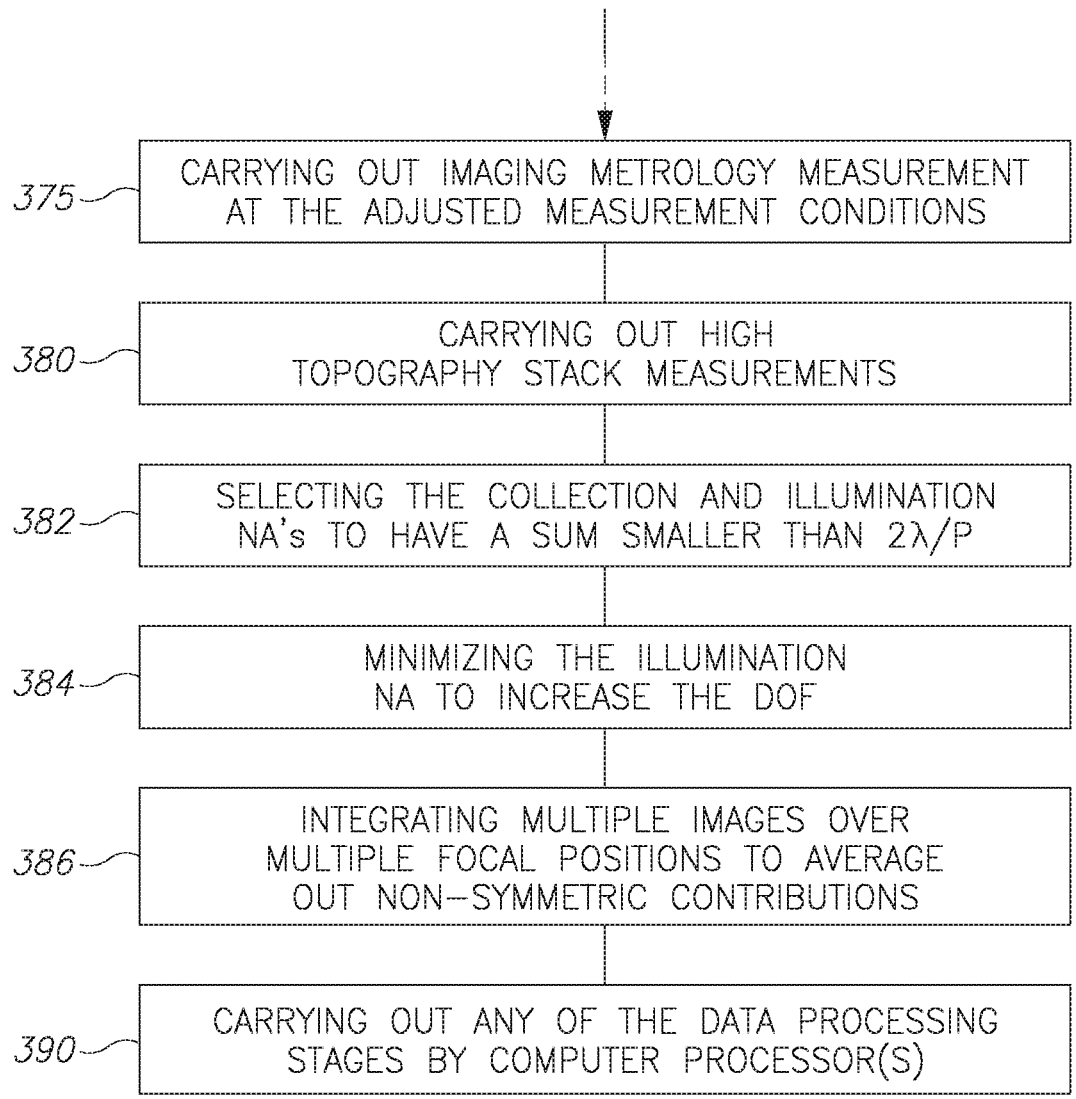
Figure 10 (cont. 3)

TOPOGRAPHIC PHASE CONTROL FOR OVERLAY MEASUREMENT

CROSS REFERENCE TO RELATED APPLICATIONS

This application claims the benefit of U.S. Provisional Patent Application No. 62/163,783 filed on May 19, 2015 and of U.S. Provisional Patent Application No. 62/222,724 filed on Sep. 23, 2015, which is incorporated herein by reference in its entirety.

BACKGROUND OF THE INVENTION

1. Technical Field

The present invention relates to the field of metrology, and more particularly, to overlay metrology.

2. Discussion of Related Art

Current methods for optical overlay measurement rely on two main technologies: Imaging and Scatterometry. In imaging, the position of periodic targets is measured in the field of view of the optical system and the overlay (OVL) is deduced from positions of targets printed in different layers. Scatterometry utilizes interference between electromagnetic (EM) waves scattered by periodic overlay marks (targets with periodic structures) printed at different layers to deduce the relative displacement of the layers. In both cases a control on amplitudes and phases of the diffraction orders of the scattered EM waves may provide a crucial effect on accuracy and precision of overlay measurement.

SUMMARY OF THE INVENTION

The following is a simplified summary providing an initial understanding of the invention. The summary does not necessarily identify key elements nor limits the scope of the invention, but merely serves as an introduction to the following description.

One aspect of the present invention provides metrology tools and methods, which estimate the effect of topographic phases corresponding to different diffraction orders, which result from light scattering on periodic targets, and adjust the measurement conditions to improve measurement accuracy. In imaging, overlay error magnification may be reduced by choosing appropriate measurement conditions based on analysis of contrast function behavior, changing illumination conditions (reducing spectrum width and illumination NA), using polarizing targets and/or optical systems, using multiple defocusing positions etc. On-the-fly calibration of measurement results may be carried out in imaging or scatterometry using additional measurements or additional target cells.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 10 is a high flowchart illustrating a method, according to some embodiments of the invention.

DETAILED DESCRIPTION OF THE INVENTION

Figure 1:
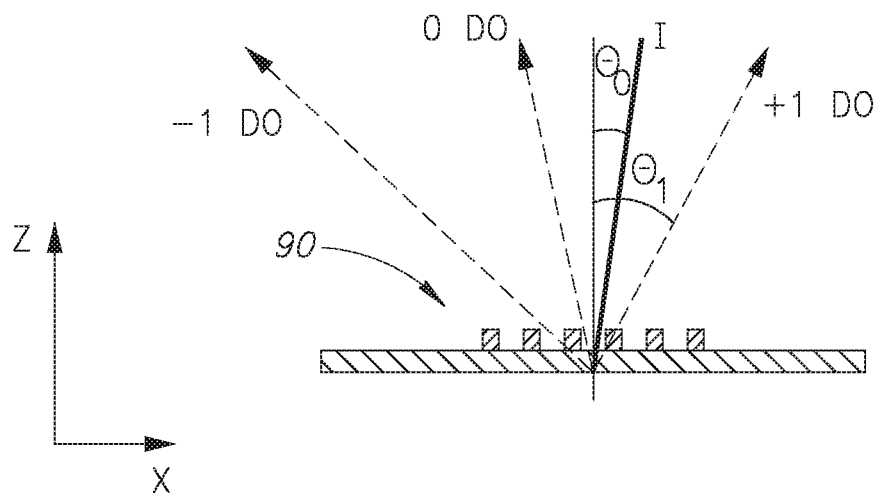
FIG. 1 is a high level schematic illustration of diffraction orders in typical imaging based overlay (IBO) metrology, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Metrology tools and methods are provided, which estimate the effect of topographic phases corresponding to different diffraction orders, which result from light scattering on periodic targets, and adjust the measurement conditions to improve measurement accuracy. In imaging, overlay error magnification may be reduced by choosing appropriate measurement conditions based on analysis of contrast function behavior, changing illumination conditions (reducing spectrum width and illumination NA), using polarizing targets and/or optical systems, using multiple defocusing positions etc. On-the-fly calibration of measurement results may be carried out in imaging or scatterometry using additional measurements or additional target cells.

Embodiments of the present invention provide efficient and economical methods and mechanisms for carrying out imaging and/or scatterometry metrology measurements with better accuracy. Metrology overlay (OVL) measurement is performed on specially designed "proxy" metrology targets having typical scales (pitches) larger than hundreds nanometers. Device design rule pitches are unresolved by imaging and scatterometry overlay optical tools and the gap between device pitch (<90 nm) and metrology target pitch increases with time. As the lithography processing steps are optimized to device scales, the metrology targets are not fully process compatible which results in all type of target asymmetries appearing in OVL targets. In most cases the geometrical asymmetry, like the asymmetry in side wall angles (SWA) of the target edges, is not large (about 1 nm) and leads to some ambiguity in the definition of OVL within allowed tolerances. However, both Imaging and Scatterometry OVL approaches under unsuccessful measurement conditions may magnify the effect of target asymmetry by order of magnitude which leads to significant errors in OVL measurements. Approaches which were considered for improving the accuracy of OVL measurement comprise (i) seeking a recipe optimization for optimal measurement conditions without any sufficient measurement tool modifications; (ii) providing a tool modification which allows OVL measurement under conditions excluding any magnification of the target asymmetry effect; (iii) using a two-beam imaging scheme which solves the problem of target asymmetry magnification but requires using a blocker in the collection pupil plane, and (iv) carrying out measurements under special illumination conditions, discussed below.

Figure 8:
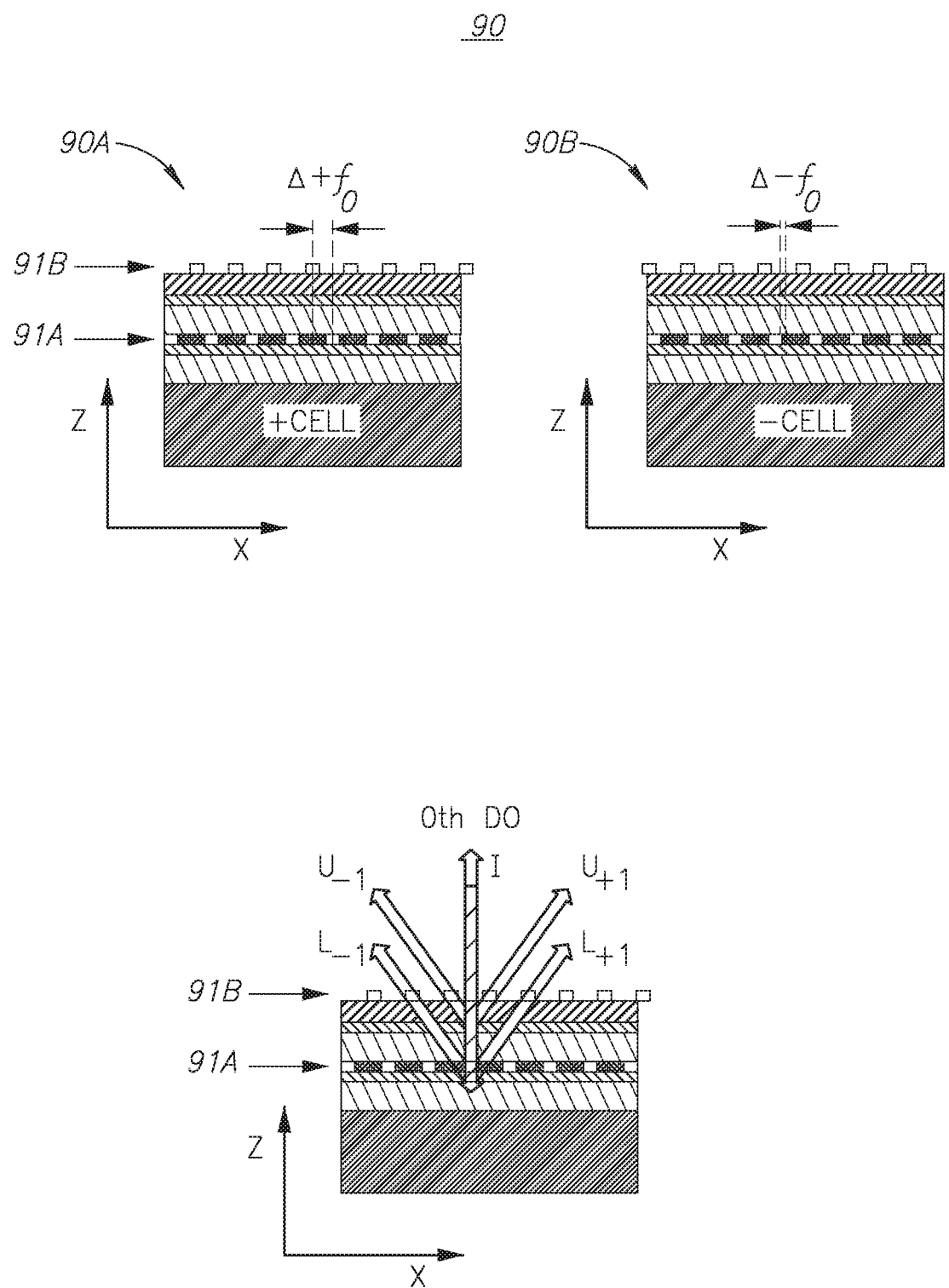
FIG. 8 is a high level schematic illustration of diffraction orders in typical diffraction based overlay (DBO) metrology, according to some embodiments of the invention.

Major parameter controlling both sensitivity and accuracy of optical Overlay metrologies for both Diffraction Based Overlay (DBO) and Imaging Based Overlay (IBO) is the phase difference between EM fields interfering to produce measured signal. FIGS. 8 and 1 are high level schematic illustrations of diffraction orders in typical DBO and IBO metrology, respectively, according to some embodiments of the invention. The topographic phase in DBO (FIG. 8, discussed below) is defined as the mean phase difference between electromagnetic (EM) fields diffracted by upper and lower gratings (91B, U and 91A, L respectively) of a SCOL target 90A, to the same diffraction orders (−1, +1). In IBO case (FIG. 1), the topographic phase controlling the measurement quality is the mean phase between zeroth order and the symmetric (e.g., $\pm 1^{st}$) diffraction orders (DO) diffracted from an imaging target 90.

Both technologies suffer of similar inaccuracy mechanism as sensitivity to asymmetries of the targets. Such asymmetries, mostly stemming in incompatibility of large pitch overlay targets to processes optimized for production of smaller pitches devices, are manifested as imbalance of both phases and amplitudes of diffraction orders. The former cannot be distinguished from grating displacement (overlay), but its effect is limited by simple geometrical ambiguity. The effect of amplitude imbalance, though, can be grossly magnified, and is controlled solely by the interference of the fields constituting the signal. The mechanism of target asymmetry amplification is described in detail in WIPO Patent Publication No. PCT/US15/62523, incorporated herein by reference in its entirety, and below. In both technologies the effect of target asymmetry increases when topographic phase behavior causes a significant signal contrast reduction for imaging OVL or differential signal reduction for scatterometry OVL. Accordingly, the control of topographic phase behavior may play a crucial role in improvement of accuracy of OVL measurement. In the following, several possibilities are disclosed for topographic phase control including modifications to measurement hardware and specialized target design, as well as various approaches for establishing of the best measurement conditions required for improvement of OVL measurement accuracy.

For example, in the IBO case (FIG. 1), an estimation of the effect of the phase difference between zero and first diffraction orders on the accuracy of OVL measurement is provided for an imaging tool with small NA (numerical aperture, NA<0.2) illumination conditions (Illumination ray denoted by I). The positions of diffraction orders in the pupil is shown in FIG. 1, where $\theta_0$ denoting the illumination angle and $\theta_1$ denoting the angle of the first diffraction order provided by scattering on a periodic structure (imaging target 90), having a period P, both with respect to a normal to the target plane. $\theta_1$ and $\theta_0$ are related in Equations 1, with $\lambda$ denoting the illumination wavelength.

$$\sin\theta_1 = -\sin\theta_0 + \frac{\lambda}{P} \Rightarrow \sin\theta_1 \cong -\theta_0 + \frac{\lambda}{P};$$

$$\cos\theta_1 = \sqrt{1 - \left(-\theta_0 + \frac{\lambda}{P}\right)^2} \cong \sqrt{1 - \left(\frac{\lambda}{P}\right)^2} + \frac{\theta_0 \frac{\lambda}{P}}{\sqrt{1 - \left(\frac{\lambda}{P}\right)^2}}$$

Equations 1

Denoting the difference of topographic phases between the first and the zeroth diffraction orders as $\Psi$, Equations 2 define the corresponding defocus $\Delta F$ needed to compensate the topographic phase $\Psi$, and the corresponding topographic phase spread in the pupil, estimated for the case that for $\lambda/P=1/2$ and $\Psi \sim \pi/2$ (worst case).

$$\frac{2\pi}{\lambda}\Delta F \cdot \left(1 - \sqrt{1 - \left(\frac{\lambda}{P}\right)^2}\right) = \Psi \Rightarrow \Delta F = \frac{\lambda \Psi}{2\pi\left(1 - \sqrt{1 - \left(\frac{\lambda}{P}\right)^2}\right)}$$

Equations 2

$$\frac{2\pi}{\lambda}\Delta F \frac{\theta_0 \frac{\lambda}{P}}{\sqrt{1 - \left(\frac{\lambda}{P}\right)^2}} = \frac{\theta_0 \frac{\lambda}{P} \Psi}{\left(1 - \sqrt{1 - \left(\frac{\lambda}{P}\right)^2}\right) \cdot \sqrt{1 - \left(\frac{\lambda}{P}\right)^2}} \cong$$

$$\frac{2\theta_0 \Psi}{\left(1 - \frac{\sqrt{3}}{2}\right)\sqrt{3}} \sim 4\pi \cdot NA$$

Even for small illumination NA~0.2, a large topographic phase spread of $\sim\pi$ means that when the central part of the illumination points is in the best contrast position, the peripheral illumination points are around the zero contrast position which leads to large magnification of the effect of target asymmetry on accuracy of OVL measurement and to the lack of possibility to control the topographic phases of scattered light may course inaccurate OVL measurement. This effect is drastically increased with larger illumination NA.

Advantageously, the disclosed systems and methods overcome the main disadvantage of the standard imaging tool and scatterometry tools, namely the uncontrollable magnification of target asymmetry effect which is present when inappropriate measurement conditions are used.

In the following, the target asymmetry contributions to the accuracy budget are analyzed in detail. The expression for the amplitude of the electric field in the image plane can be written as in Equation 4, with f, g being the pupil coordinates, which relate to the actual dimensional pupil coordinates $$\xi, \eta \text{ as } f = \frac{\xi}{R}\frac{NA}{\lambda}, g = \frac{\eta}{R}\frac{NA}{\lambda},$$

where R is the lens radius, E(f, g) is the amplitude of the electric field in the pupil plane and $e^{2\pi i(1-\cos\theta)\Delta z/\lambda}$ describes the effect of defocusing $\Delta z$ on the amplitude of the electric field in the pupil plane.

$$E(x, y) = \iint_{\sqrt{f^2+g^2} \leq \frac{NA}{\lambda}} E(f, g) \cdot e^{2\pi i(1-\cos\theta)\Delta z/\lambda} \cdot e^{-2\pi i(fx+gy)} df dg$$

Equation 4

In the most simple, non-limiting, optical configuration with only the ±1 and 0 diffraction orders being captured by lens, Equation 4 can be simplified into Equation 5, with P denoting the target pitch in the X direction, with $a_0$, $a_1$ and $a_{-1}$ being complex amplitudes of diffraction orders (depending on process variations and target asymmetries), GP denoting the grating position and $\Delta F$ denoting the defocus.

$$E(x) = a_0 e^{i\frac{2\pi\Delta F}{\lambda}[1-\cos(\theta_0)]} +$$

$$a_1 e^{i\frac{2\pi}{P}(x-GP) + \frac{2\pi\Delta F}{\lambda}[1-\cos(\theta_1)]} + a_{-1} e^{i\frac{2\pi}{P}(x-GP) + i\frac{2\pi\Delta F}{\lambda}[1-\cos(\theta_{-1})]}$$

Equation 5

Figure 2A:
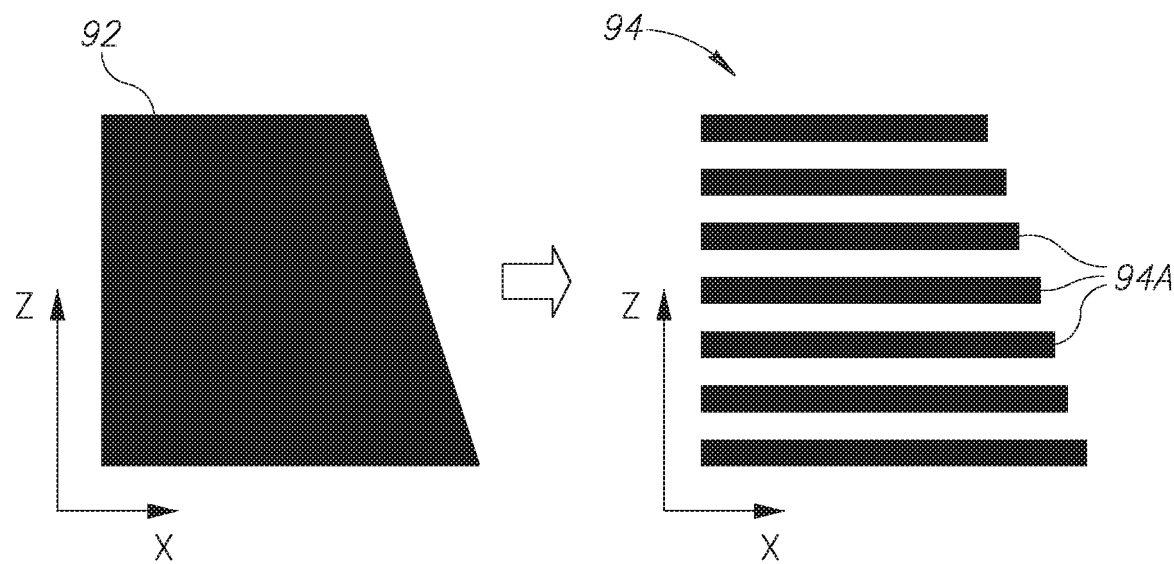
FIG. 2A is a high level schematic illustration of an approximation of an asymmetric grating with a small sidewall angle on the right side by a structure that is a sum of symmetric rectangular areas with different centers, according to some embodiments of the invention.

FIG. 2A is a high level schematic illustration of an approximation of an asymmetric grating 92 with a small side-wall angle on the right side by a structure 94 that is a sum of symmetric rectangular areas 94A with different centers, according to some embodiments of the invention. The scattering off asymmetric grating 92 is approximated as the sum of scatterings from areas 94A in structure 94.

The amplitude of each diffraction order is a sum of plane waves corresponding to scattering from different rectangular areas 94A. For example, Equations 6 express the amplitudes $A^{(1)}$, $A^{(-1)}$ for the ±1 first diffraction orders, with $A_0^{(1)}$ denoting the amplitude of the first diffraction order without target asymmetry, $A_n^{(1)}$ denoting the amplitudes from areas 94A and $\delta_{Re}^{(1)} + i\delta_{Im}^{(1)}$ denoting the effect of target asymmetry on the amplitude of the first diffraction order. $\Delta_n$ denotes the extension of the $n^{th}$ area relative to the nominal area length corresponding to the grating without asymmetry and $\psi_n$ denotes the topographic phase of the $n^{th}$ area.

$$A^{(1)} =$$

$$\sum_n A_n^{(1)} \cdot e^{i\psi_n + 2\pi i \frac{x+\Delta_n/2}{P}} \cong \sum_n A_n^{(1)} \cdot e^{i\psi_n + 2\pi i \frac{x}{P}} \left(1 + \pi i \frac{\Delta_n}{P}\right) =$$

$$A_0^{(1)} e^{i\psi^{(1)} + 2\pi i \frac{x}{P}} (1 + \delta_{Re}^{(1)} + i\delta_{Im}^{(1)})$$

$$A^{(-1)} = A_0^{(-1)} e^{i\psi^{(-1)} - 2\pi i \frac{x}{P}} (1 - \delta_{Re}^{(-1)} - i\delta_{Im}^{(-1)})$$

Equations 6

Under normal illumination condition, Equation 7 expresses simplifications of Equations 5 and 6, with $$\sin\theta_1 = \frac{\lambda}{P}$$

and $$\Delta\psi = \psi^{(1)} - \psi^{(0)} - 2\pi(1 - \cos\theta_1)\Delta z/\lambda$$

and assuming $A^{(1)} = A^{(-1)}$, $\psi^{(1)} = \psi^{(-1)}$, $\delta_{Re}^{(1)} = \delta_{Re}^{(-1)}$, $\delta_{Im}^{(1)} = \delta_{Im}^{(-1)}$ and the corresponding field intensity, approximated to the leading order (neglecting for simplicity the square of first diffraction orders amplitudes):

$$E(x) \sim$$

$$A^{(0)} e^{i\psi^{(0)}} + A_0^{(1)} e^{i\psi^{(1)} - 2\pi i(1-\cos\theta_1)\Delta z/\lambda} \left[(1 + \delta_{Re} + i\delta_{Im})e^{2\pi i \frac{x}{P}} + \right.$$

$$\left. (1 - \delta_{Re} - i\delta_{Im})e^{-2\pi i \frac{x}{P}}\right] ==$$

$$A^{(0)} e^{i\psi^{(0)}} + 2A_0^{(1)} e^{i\psi^{(1)} - 2\pi i(1-\cos\theta_1)\Delta z/\lambda} \left[\cos\left(2\pi \frac{x}{P}\right) + \right.$$

$$\left. i \cdot (\delta_{Re} + i\delta_{Im})\sin\left(2\pi \frac{x}{P}\right)\right] \sim \sim$$

$$A^{(0)} + 2A_0^{(1)} e^{i\Delta\psi} \left[\cos\left(2\pi \frac{x}{P} - \delta_{Im}\right) + i \cdot \delta_{Re}\sin\left(2\pi \frac{x}{P}\right)\right]$$

$$I(x) \cong \text{Constant} + 2A^{(0)} A_0^{(1)} \cos(\psi^{(1)} - \psi^{(0)} -$$

$$2\pi(1 - \cos\theta_1)\Delta z/\lambda) \cdot \cos\left[\frac{2\pi}{P}x - \delta_{Im} - \right.$$

$$\left. \delta_{Re} \cdot \tan(\psi^{(1)} - \psi^{(0)} - 2\pi(1-\cos\theta_1)\Delta z/\lambda)\right]$$

Equations 7

In terms of Equation 7, due to the target asymmetry there is a natural ambiguity in the position of the target center, in the order of magnitude of $$\Theta\left(\frac{P}{2\pi}\{\delta_{Re}, \delta_{Im}\}\right)$$

However, wrong tool measurement conditions may magnify this target geometrical ambiguity by a factor of $\tan(\psi^{(1)}-\psi^{(0)}-2\pi(1-\cos\theta_1)\Delta z/\lambda)$. This factor is almost zero in the best contrast position but goes to infinity in the zero contrast position. The value of this factor can be controlled by a correct choice of the measurement focus position, however, the following issues are encountered: (i) Each illumination pupil position and each wavelength provide their own topographic phase and, correspondingly, their own best contrast focus position. Since the field image is a sum of images corresponding to different illumination points and wavelengths it may collect images for which the target asymmetry effect is strongly magnified. This first issue can hardly be solved by changing the measurement focus position since for relatively large illumination NA the spread of best contrast positions corresponding to different illumination angles can be as large as micron. Since the distance between the measured focus position and the best contrast positions of a part of illumination angles can be as large as half a micron, there is target accuracy magnification in any chosen measurement focus position. (ii) The best contrast position varies with process variations. In case the focus acquisition procedure provides a measurement focus position which is not strongly correlated with the best contrast position, it becomes an additional factor that deteriorates OVL measurement accuracy.

Figure 2B:
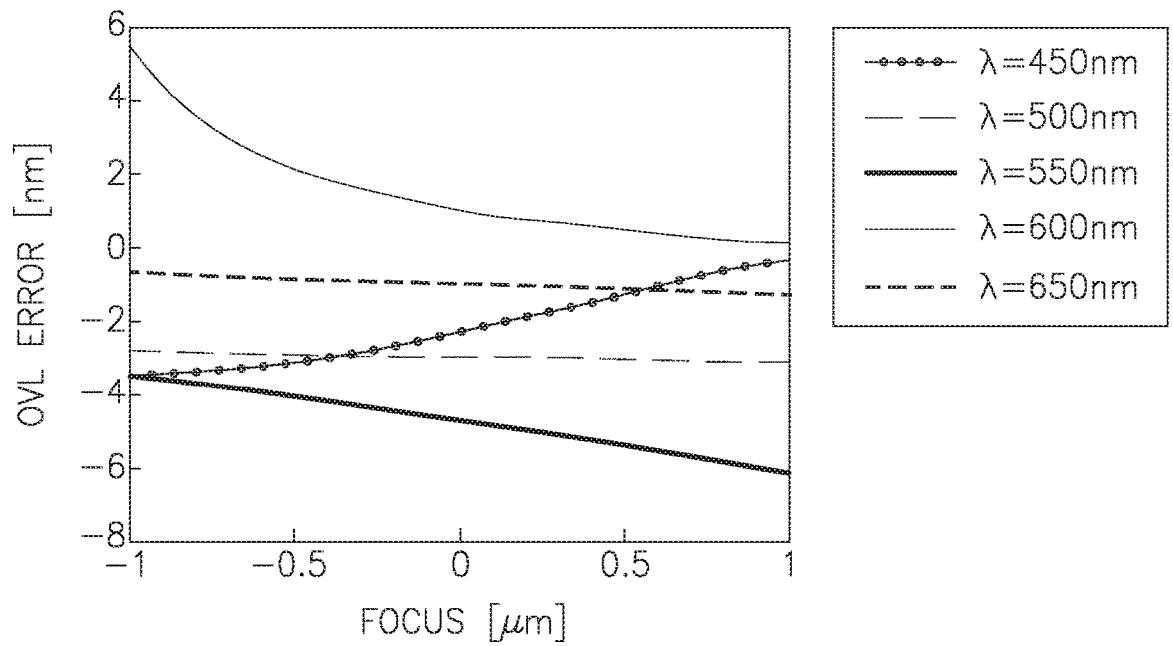
FIGS. 2B and 2C schematically illustrate exemplary simulation results for the model in FIG. 2A, relating the overlay error with the defocusing, according to some embodiments of the invention.
Figure 2C:
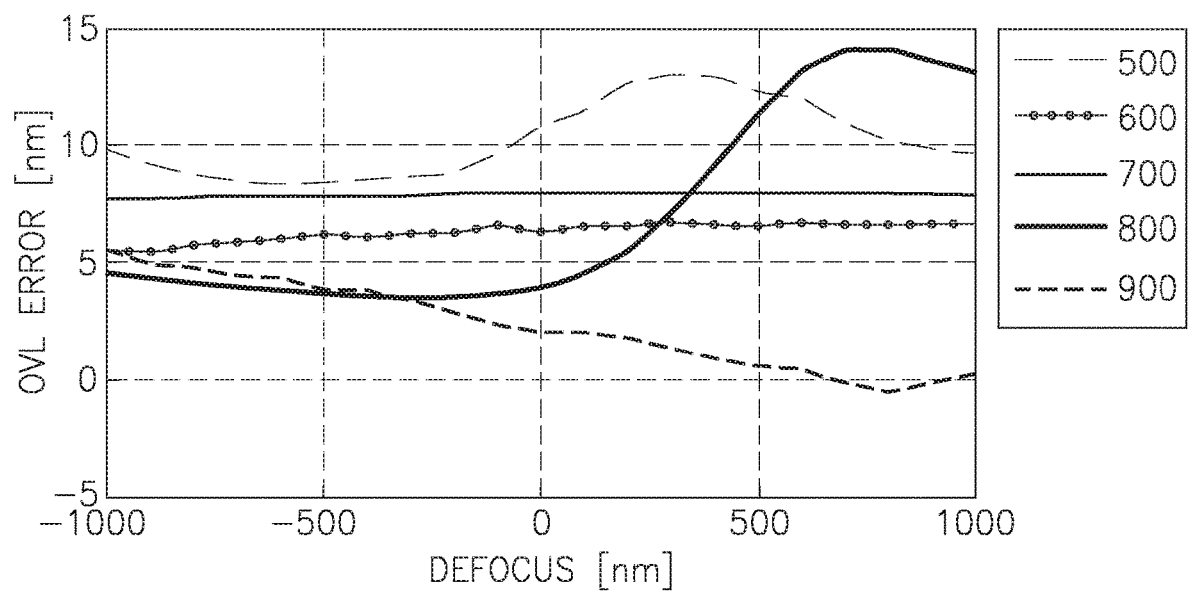

These issues are exemplified in simulations, assuming SWA=88° (corresponding to <±1 nm OVL ambiguity for a layer height<100 nm), resulting in the relations shown in FIG. 2B, in which for certain measurement conditions (e.g., λ) and measurement focus position, the imaging tool provided OVL error within the range of ±5 nm, i.e., the imaging tool enhanced the OVL error originating from the SWA by a factor of 5, under the specific simulated conditions. FIG. 2C illustrates another simulation example, showing even larger magnification factors.

Proposed solutions comprise any of the following approaches: (i) an appropriate choice of measurement conditions for which the best contrast focus position coincides with grating position (ii) Reduction of the spectral range and the illumination NA, (iii) Grabbing several images in different focus positions on each site and finding the best focus position, (iv) Using large illumination wavelengths, and (v) simultaneous grabbing of several images in different focus positions. These approaches are discussed below in detail.

Figure 2D:
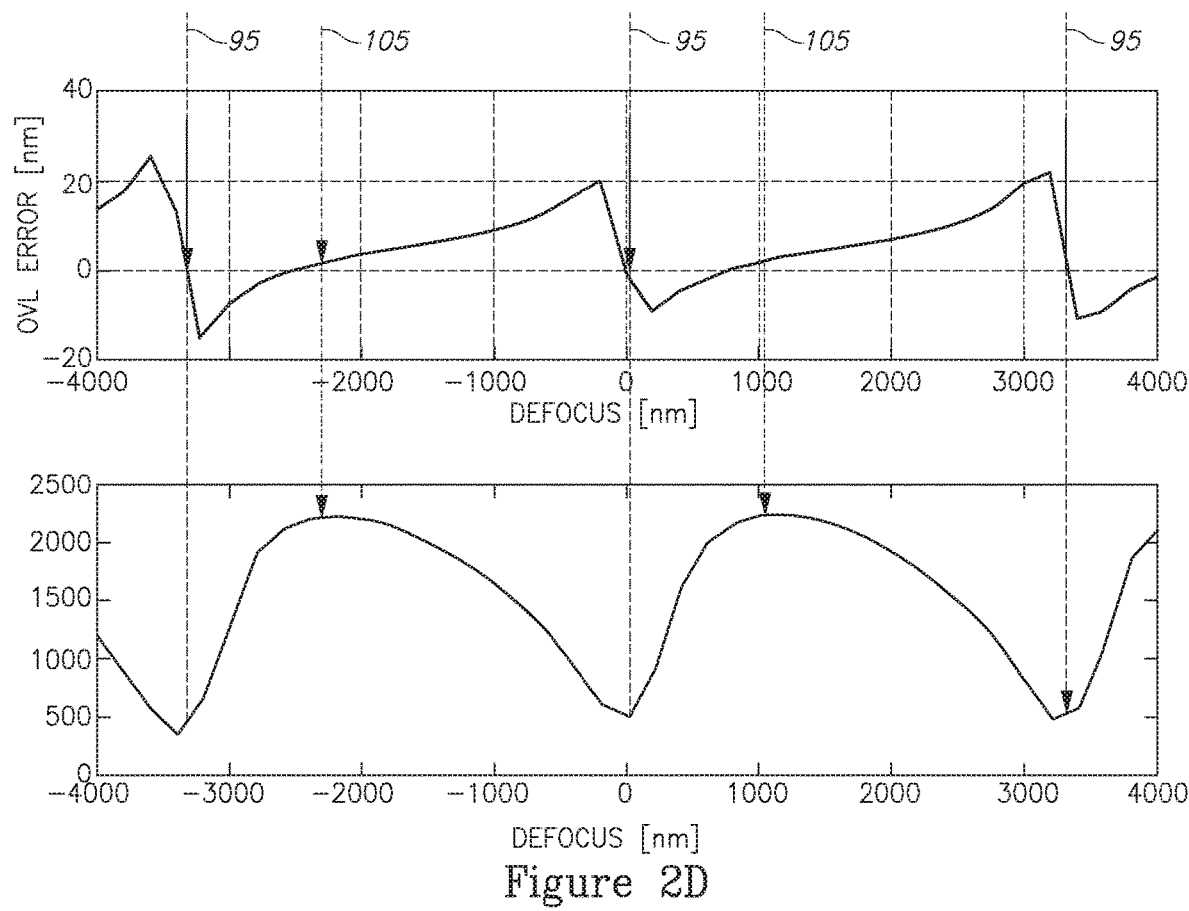
FIG. 2D schematically illustrates exemplary simulation results for using a small illumination numerical aperture, relating the overlay error to the contrast function, according to some embodiments of the invention.

Radically reducing the spectral range (e.g., below 10 nm) and the illumination NA (e.g., below NA~0.1) (approach (ii)) reduces the spread of best contrast positions to 200-300 nm. FIG. 2D illustrates simulation results using a small illumination NA of 0.1 in which points 105 are identified as the best contrast positions with low OVL error magnification and points 95 are identified as zero contrast positions. As illustrated in FIG. 2D, the OVL error is small and changes slowly with focus changes around the best contrast position (105) while the OVL error varies much more strongly with focus changes around the zero contrast position (95). Positions 105 and 95 represent different types of zero OVL error measurement points—in zero contrast position 95 the zero OVL error results from the fact that amplitude of the first harmonic is exactly zero and the OVL is measured with the second harmonic, which is usually much smaller than the amplitude of the first harmonic. The measurement at zero contrast position 95 is discussed below and requires hardware (HW) modifications of the metrology tool (e.g., a zero order blocker in the collection path, as illustrated in FIG. 3A).

Figure 3A:
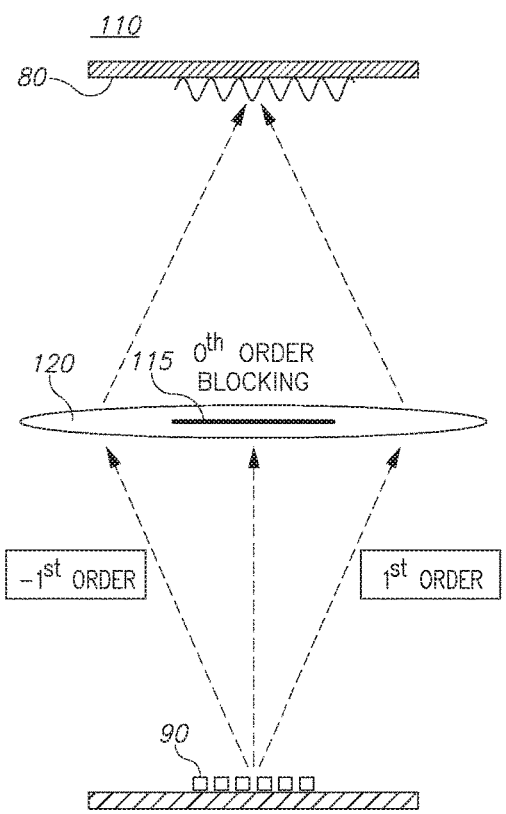
FIG. 3 is a high level schematic illustration of a corresponding optical system, according to some embodiments of the invention.
Figure 3A:
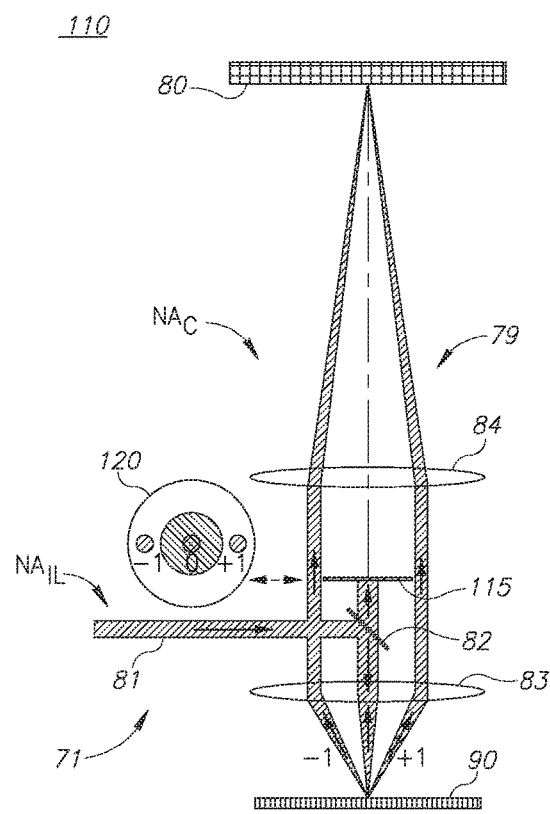

FIG. 3A is a high level schematic illustration of a theoretical model and an optical system 110, according to some embodiments of the invention. Illumination 81 (in illumination path 71) enters system 110 and directed via optics 82 (e.g., a beam splitter) and objective 83 onto target 90, from which diffraction signals are collected and directed via beam splitter 82 and optics 84 (e.g., a tube lens) (in collection path 79, also termed detection path) to a detector 80 (e.g., a CCD—charge coupled device). A spatial filter 115 may be introduced to block the zeroth order diffraction signal, ideally at the Fourier plane (pupil plane 120). In a non-limiting manner, only the first diffraction orders are illustrated.

System 110 may be configured according to the following guidelines to reduce or cancel accuracy error magnification: a low-NA source such as a laser may be used to provide relaxed requirements for light uniformity; only first order diffraction may be passed to provide clean two-beam interference and large depth-of-focus; both process and resist signals (i.e., diffraction signals from the different target layers) may be passed through the same part of pupil plane 120 to cancel aberrations; and focusing may be carried out on the fly, noting that good image contrast allows measurement without implementing adaptive noise reduction algorithms (ANRA) to achieve a short MAM (move-acquire-measure) time, e.g., under 200 msec.

In particular, the following disclosed algorithmic approach overcomes difficulties related to the introduction of opaque zero order blocker 115 and involved in the requirement for good separation of the diffraction orders in the collection pupil, to avoid either leakage of the zeroth order into the image, or sharp truncation of higher DOs. The inventors note that this requirement limits the minimal target size to be above 10-15 um to provide small diffraction tails. On the other hand, the very limited size of zero order blocker 115 requires very small illumination NA causing a light budget problem. In particular, the reduction of the illumination NA beyond a particular threshold value (van Cittert-Zernike theorem) gives rise to spatially extended coherence effects (ringing) distorting the image. However, the inventors have found out that the following algorithm, while maintaining the advantages inherent in the optical scheme illustrated in FIG. 3A, overcomes the above-listed limitations by not using zero order blocker 115, possibly requiting minor hardware modifications, thereby achieving a superior accuracy in imaging OVL measurement, improves tool performance and reduces effect of process variations. In particular, the inventors have found out that selecting only even harmonics for OVL measurement and/or using through-focus averaging to reduce the contribution of even diffraction orders to the even signal harmonics—provide these advantages, as explained below.

Figure 3B:
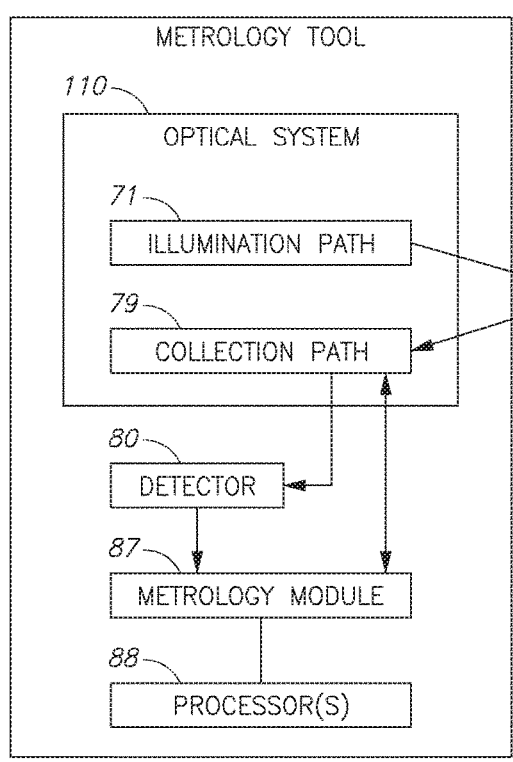
Figure 3C:
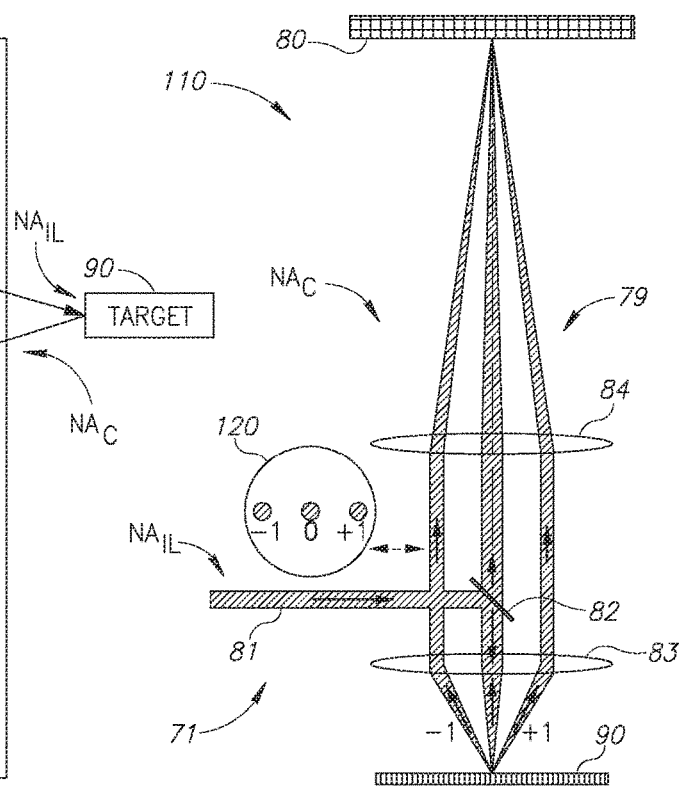

FIGS. 3B and 3C are high level schematic illustrations of metrology tool 85 and optical system 110, respectively, according to some embodiments of the invention. Metrology tool 85 is illustrated schematically as comprising optical system 110 with illumination path 71 and collection path 79 with corresponding illumination and collection numerical apertures ($NA_{IL}$ and $NA_C$, respectively), detector 80 and metrology module(s) 87 associated with processor(s) 88. Optical system 110 is illustrated schematically as in FIG. 3A, but without zero order blocker 115, and configured for carrying out high topography stack measurements wherein collection and illumination numerical apertures thereof are selected to have a sum smaller than 2λ/P, and/or optical system 110 is configured to integrate multiple images captured thereby over multiple focal positions thereof, to average out non-symmetric contributions—as explained below. Under such configurations, metrology tool 85 and optical system 110 mimic the two-beam configuration disclosed herein above and below, yet avoid zero order blocking by including only the second harmonic with specific λ/P ratios as explained below.

The main requirements for the disclosed optical scheme are (i) adjustable illumination spectral range and collection NA ($NA_C$) to make sure that for any chosen target pitch objective lens 83 collects only the zeroth and ±1 (first) diffraction orders; and (ii) a relatively small illumination NA (to provide large DOF (depth of focus). Specifically, $NA_C$ and $NA_{IL}$ may be selected to satisfy the condition 2λ/P>$NA_C$+$NA_{IL}$ with λ denoting the illumination wavelength and P denoting the grating pitch (of target 90). Under such conditions, the second harmonic of the measured signal is formed as a result of interference between ±1 diffraction orders only, and in this sense it is fully equivalent to the signal measured with zero order blocker 115 (apart from the precision issues which should be solved by other hardware means).

Concerning the DOF, after scattering on target 90, the oblique plain waves are the ±1 diffraction orders propagating at angles defined by $\sin(\vartheta_{-1})=-\sin(\vartheta_0)\pm\lambda/P$, with $\vartheta_0$ denoting the illumination angle. In the case of zero illumination NA ($NA_{IL}=0$) and exact fulfillment of a normal illumination condition ($\vartheta_0=0$), it follows that $\cos(\vartheta_i)\equiv\cos(\vartheta_i)$ and the relative phase between the two plane waves doesn't change with focus, i.e., corresponding to infinite DOF. Due to the finite size of the illumination ring, the normal illumination condition can only be satisfied approximately. However, as in this case the DOF is determined by the illumination NA ($NA_{IL}$) rather than by the collection NA ($NA_C$) as in a general case, it can be shown that the value of DOF for small illumination NA can be approximated as $$DOF \cong \frac{P\sqrt{1-(\lambda/P)^2}}{2.5\cdot NA_{IL}}.$$

For example, for P=1800 nm, λ/P~0.5 and $NA_{IL}$=0.2 yields a DOF>3 μm, which allows measurement of high topography stacks with a single grab.

Alternatively or complementarily, multiple images may be integrated over multiple focal positions to average out the non-symmetric contributions. Deep stack single grab measurements may be implemented with large DOF of the interference pattern between ±1st orders (or any other symmetric pair of orders). The averaging utilizes the contrast reversal of interference between any non-symmetric DOs pair as the object (target 90) moves through focus, while interferences between symmetric orders do not change the contrast sign. Integration may be implemented by software and/or by hardware, allowing focus measurement during the exposure. In such way, single grab deep stack measurement may be conducted disregarding the wavelength to pitch ratio and collection NA.

Concerning the accuracy, as shown above and below, the mechanism of target asymmetry amplification (the main source of OVL measurement inaccuracy) is connected to the value of topographic phase difference between the diffraction orders forming the image. The most accurate measurement is done when the phase difference between diffraction orders corresponding to normal illumination condition is almost zero. This condition is automatically satisfied for image formed by interference between ±1 diffraction orders, providing high accuracy.

Returning to the five approaches presented above, grabbing a few images in different focus positions (e.g., three images as a non-limiting example) on each site (approach (iii)) may be used to find the best contrast position on the fly (see last point in approach (ii)) using, for example, a parabolic approximation of contrast values calculated for each grabbed image. Since the inaccuracy magnification factor changes its sign around the best contrast position (at points 105, 95 in FIG. 2D), an accurate OVL measurement can be obtained combining OVL values calculated for images with focus positions on different sides with respect to the best contrast position using appropriate weights. This approach provides a solution for site to site process variations.

Using large illumination wavelengths (approach (iv)) allows extension of the spectral range and the illumination NA since the rate of topographic phase change with wavelength and illumination angle is drastically reduced. This approach requires large pitches, e.g. around 2000 nm.

Simultaneous grabbing of several images in different focus positions (approach (v)) may be used to overcome the difficulty arising from the fact that since the OVL is measured between two layers having different best contrast positions, the most accurate measurement can be achieved if the center of symmetry position for each layer is measured in its own best contrast position. In this case the synthetic kernel (or synthetic OVL value as a result of interpolation to the focus position corresponding to the best focus position for this layer) is a different combination of signals corresponding to each one of the grabbed images. Accordingly, the resulted OVL includes the effect of the stage motion during the grabbing of images which may affect the precision of OVL measurement. In order to eliminate this effect from OVL measurement approach the imaging tool optical configuration may be changed to allow simultaneous grabbing of several images in different focus positions. The details of one possible implementation of approach (v) are described below.

Grabbing of the targets printed at each one of the layers of interest in its own best contrast focus (approach (v)) advantageously provides process robust measurements of multilayered targets, which ensures, under conditions of small enough illumination NA and sufficiently narrow illumination bandwidth, the cancellation of topographic phases that are responsible for sensitivity of the measurements to process variations.

Figure 4A:
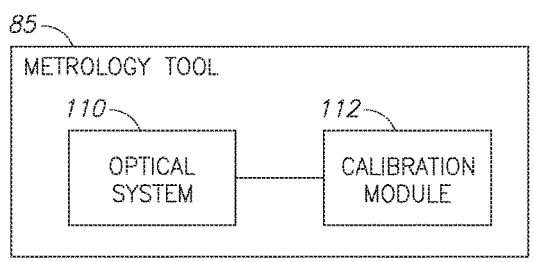
FIGS. 4A-4C are high level schematic illustrations of optical systems for simultaneous measurement of multiple focus positions, according to some embodiments of the invention.
Figure 4B:
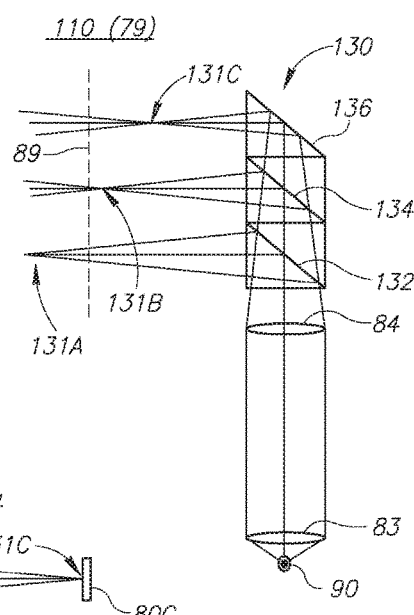
Figure 4C:
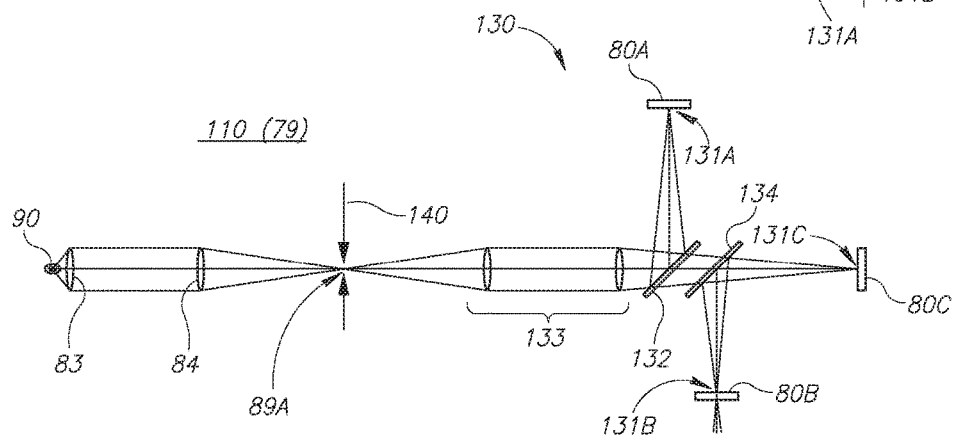

FIGS. 4A-4C are high level schematic illustrations of optical systems 110 for simultaneous measurement of multiple focus positions, according to some embodiments of the invention. FIG. 4A is a high level schematic illustration of an imaging metrology tool 85 having optical system 110 and a calibration module 112 associated therewith, and possibly operated by one or more processor(s) (see FIG. 9).

Calibration module 112 may be configured to derive a dependency of an overlay error magnification on a level of defocusing and optical system 110 may be configured to operate at a narrow spectral range, Δλ≤10 nm, at a narrow illumination numerical aperture, NA≤0.1, and at a focus position that corresponds to zero overlay error magnification according to the derived dependency (see approach (ii) above).

Optical system 110 may be, alternatively or complementarily, configured to grab a plurality of metrology target images at a corresponding plurality of focus positions, and calibration module 112 may be configured to estimate an inaccuracy magnification factor of the grabbed images and determine a best contrast position by identifying a sign change of the inaccuracy magnification factor with respect to the focus positions, with imaging metrology tool 85 being re-configured to be operated at the determined best contrast position (see approach (iii) above). Calibration module 112 may be configured to operate on-the-fly during regular metrology tool operation.

Optical systems 110 may be configured to enable simultaneous measurement of target 90 in multiple de-foci (focus locations), while calibration module 112 in metrology tool 85 (FIG. 4A) may be configured to provide a particular per-layer grab centering without risk of compromised precision (see approach (iv) above).

Optical system 110 may have a first detection focus location 131C of a collection path 79 (schematically illustrated by objective 83 and optics 84) in metrology tool 85 and comprise at least two beam splitting elements 132, 134 along collection path 79 which are positioned to provide at least two corresponding additional focus locations 131A, 131B having different collection path lengths than first detection focus location 131C.

For example, optical system 110 may comprise (FIG. 4B) an optical assembly 130 comprising beam splitters 132, 134 (e.g., BS 30/70 and BS 50/50 respectively) followed by a mirror 136 configured to provide three respective focal locations (foci) 131A-C approximately at detection plane 89. The exemplary configuration of optical assembly 130 provides three images having equal power and corresponding to the three different focus locations, which may be detected by same detector 80 without any mechanical drift. Optical system 110 may thus be designed to have a static multi-grab architecture. Quantification of the parameters in optical system 110, defining $\Delta Z_o$ as the longitudinal displacement of the object, $\Delta Z_i$ as the longitudinal displacement of the image, M as the magnification of the imaging system and $n_o$ and $n_i$ as the refractive indexes correspondingly in the object and image media, is provided by Equations 8 and exemplified for use typical dimensions of metrology targets 90, namely lateral dimensions of L=30 µm and magnification of 125, without overlap between images, to provide the minimal $\Delta Z_o$ that can be measured in optical system 110 illustrated in FIG. 4B.

$$\frac{\Delta Z_i}{\Delta Z_o} = \frac{n_i}{n_o} M^2;$$

$$\frac{L}{M} = \Delta Z_o = 240 \text{ nm}$$

Equations 8

In another example, optical system 110 may comprise (FIG. 4C) an optical assembly 130 comprising a reticle 140 at a field stop (e.g., a plane 89A equivalent to detector plane 89), optics 133 and beam splitters 132, 134 configured to provide three respective focal locations (foci) 131A-C, e.g., detected by three corresponding detectors 80A-C. Detectors 80A-C may be separate and capture images at different axial displacements or may be at least partially unified and enable simultaneous imaging of targets from different wafer layers (double or more grab).

Reticle 140 is being illuminated mainly by the specular reflection of illumination light 81 from the wafer (target 90), so that the illumination NA of reticle 140 ($NA_{reticle}$) can be estimated in terms of the illumination NA ($NA_{ill}$), and the range of foci ($\Delta Z_o$) coverable with optical system 110 illustrated in FIG. 4C, as expressed in Equations 9, using the known estimation of the depth of field $\Delta Z = \lambda / NA_{reticle}^2$.

$$NA_{reticle} = \frac{NA_{ill}}{M};$$

$$\Delta Z_o = \frac{\Delta Z_i}{M^2} = \frac{\lambda}{NA_{ill}^2}$$

Equations 9

For example, using exemplary data $\lambda=700$ nm and $NA_{ill}=0.2$ yields de-focus range of $\Delta Z_O=17.5\mu$ which is satisfactory for covering focal differences between targets of several layers. Optical systems 110 such as illustrated in FIG. 4C overcome the requirements for the mechanical stability of lateral positions of the detector that may be e.g., 100 nm, to maintain tolerable precision (1 nm) while using separate images to detect displacement of each one of the separate target layers. Reticle 140 in the field stop serves as a mutual reference center for determination of displacements of each one of the layers in the images.

Advantageously, proposed configurations of multi-grab through-focus measurements architecture overcome disadvantages in prior art autofocus techniques such as (i) measurement of all sites across wafer at a constant offset from the interferometric focus and (ii) sequential multi-grab acquisition of multiple images through focus, followed by separate determination of current and process layers' targets positions, for later calculation of overlay between those. Both methodologies suffer significant disadvantages. Method (i) relies on the uniformity of all process parameters across the wafer and has been shown to miss the best contrast focus positions by hundreds of nanometers, which, in turn leads to multiple nanometers of inaccuracy in overlay determination. Method (ii) suffers significant precision challenges due to involuntary drift of stage between image acquisitions, reaching several nanometers.

The new optical configuration allow achieving a superior accuracy in imaging OVL measurement, improves tool performance and reduces effect of process variations. In particular, the imaging configuration has a small illumination NA and a narrow spectral range, uses a new on-the-fly OVL measurement algorithm based on a few simultaneous images grabbed in different focus positions, and/or introduces changes in the optical configuration allowing on-the-fly alignment of images corresponding to different focal positions. The invention may be implemented in any existing metrology platform for use in OVL control.

Returning to FIG. 1, additional ways are disclosed for gaining topographic phase control in imaging OVL: (i) polarizing targets, (ii) wavelength control and (iii) interferential control.

Figure 5A:
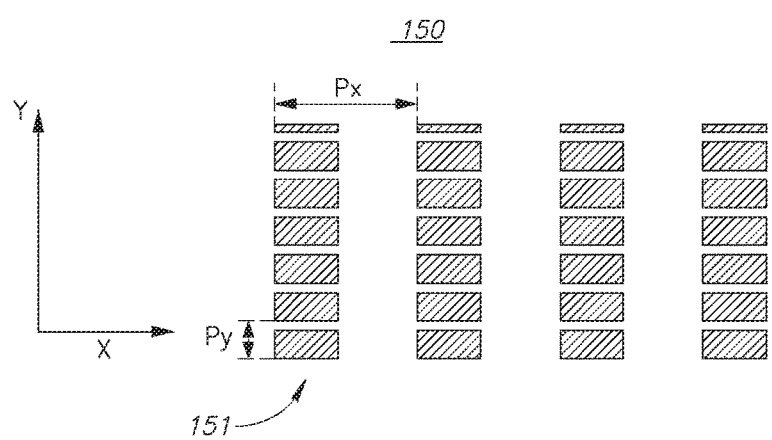
FIG. 5A is a high level schematic illustration of polarization control targets, according to some embodiments of the invention.

FIG. 5A is a high level schematic illustration of polarization control targets 150, according to some embodiments of the invention. Certain embodiments comprise imaging metrology target 150 comprising at least one periodic structure having elements 151 at a pitch p ($p_x$) along a measurement direction (X), wherein elements 151 are segmented at an unresolved pitch ($p_y$) along a direction (Y) perpendicular to the measurement direction (X). The unresolved pitch ($p_y$) is selected to provide a topographic phase of target 150 which is an integer multiple of $\pi$, as explained below.

Polarization control targets 150 (i) may be designed to provide a different responses to horizontal and vertical polarizations of the electromagnetic field (denoted as X and Y with respect to the target periodicity direction), for example using a small segmentation pitch Py which is sub-resolved by the measurement tool.

For example, in case the main axes of the plane of incidence coincides with the main axes of target 150 the effective permittivity of the lines (or trenches) 151 segmented with unresolved pitch $P_y$ may be described using the effective medium approximation as being effectively equivalent to an anisotropic film with the directional permittivity vector expressed in Equations 10, with $\varepsilon_1$ being the permittivity of one material, $\varepsilon_2$ being the permittivity of another material, $\eta$ being the duty cycle of the segmentation in the y direction and $\varepsilon_x \neq \varepsilon_y$.

$$\varepsilon_x = \varepsilon_z = \frac{\varepsilon_1 + \eta \varepsilon_2}{1 + \eta};$$
$$\varepsilon_y = \frac{\varepsilon_1 \cdot \varepsilon_2 (1 + \eta)}{\varepsilon_2 + \eta \varepsilon_1}$$

Equations 10

Figure 5B:
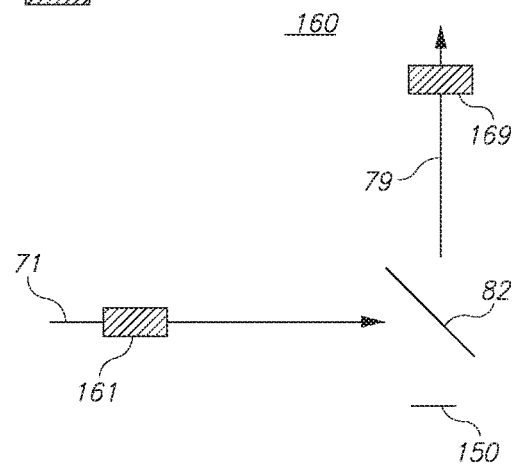
FIG. 5B is a high level schematic illustration of an optical system, according to some embodiments of the invention.

Any of a plurality of possible target designs providing different responses to vertical and horizontal polarizations of the electric field may be selected. The actual segmentation pitch may be selected based on simulations and/or on measurements of topographic phases on test wafers targets with different parameters. FIG. 5B is a high level schematic illustration of an optical system 160, according to some embodiments of the invention. In optical system 160 of a metrology tool, the direction of the linear polarization may be used to change the phase between diffraction orders of the light scattered from target 150. Optical system 160 may also comprise a polarizer 161 in illumination path 71 (e.g., providing circular light polarization, e.g., using a wave plate with different angle and retardation parameter) and an analyzer 169 in the collection path 79 to provide more effective control of the topographic phases of scattered light by changing the angle of analyzer 169 in the case of targets responding differently to different polarization conditions of illumination light 81.

Alternatively or complementarily, (ii) the illumination wavelength may be modified to control the topographic phase. The inventors have found out that changing the wavelength in ca. 50 nm for the most stacks provides contrast reversal which is equivalent to change of $\pi$ in the topographic phase. Accordingly, even small shifts of illumination spectrum of ca. ±10 nm may be used to provide significant changes in the topographic phase—making spectral control an additional factor which may be used to improve OVL measurement conditions. Moreover, since resist and process layers can be measured with different wavelengths (double grab as an example shown above), the topographic phase correction can be carried out independently for resist and process layers.

Figure 6:
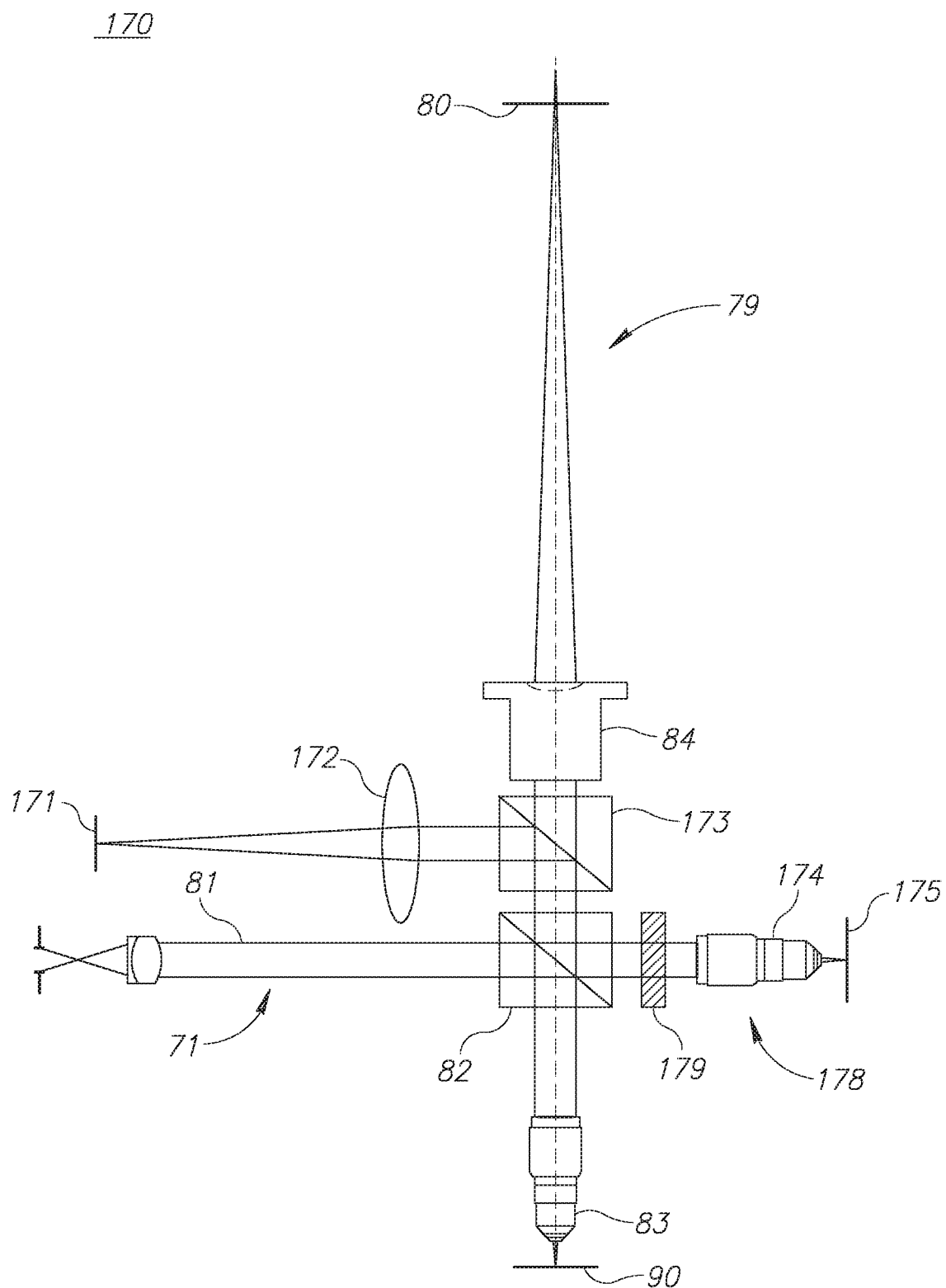
FIG. 6 is a high level schematic illustration of an optical system, according to some embodiments of the invention.

FIG. 6 is a high level schematic illustration of an optical system 170, according to some embodiments of the invention. Optical system 170 may be used in imaging metrology tools for OVL measurement. Optical system 170 comprises an adjustable reference path 178 having a reference signal integrated in a collection path 79 of optical system 170. Reference path 178 is configured to provide an adjustable phase of the reference signal optical system 170 is configured to adjust the phase of the reference signal to modify a topographic phase of an imaging metrology target to be an integer multiple of $\pi$. Adjustable reference path 178 may be integrated as a Linnik interferometer with a reference objective 174 identical to a main objective 83 of imaging metrology optical system 170 and an adjustable mirror 175, as explained in detail below.

Optical system 170 comprises illumination path 71, main objective 83 and collection path 79, and further comprises reference path 178 having a reference signal with controllable amplitude and phase which are configured to minimize a difference of topographic phases between zeroth and first order diffraction signals from at least two target layers of target 90. Illumination and collection paths 71, 79 may be associated with objective 83 via beam splitter 82 and reference path 178 may be integrated in optical system 170 via beam splitter 82. Reference path 178 may comprise objective 174 identical to main objective 83 with mirror 175, as well as associated illumination source 171 and optics 172, 173 (e.g., focusing lens 172 and beam splitter 173), in exemplary embodiments in a Linnik interferometer configuration. The amplitude of the reference signal may by controlled by an attenuator 179, e.g., by a neutral density (ND) filter and objective 174 and/or mirror 175 may be moved to control the phase of the reference signal. The resulting zero diffraction order field appears as a coherent sum of the zero diffraction orders reflected from the first and second layers of wafer (gratings of target 90) denoted $A \cdot e^{i\alpha}$ and $B \cdot e^{i\beta}$; and the zero diffraction order reflected from reference mirror 175, denoted $C \cdot e^{i\gamma}$. Accordingly, the zero order fields can be described as expressed in Equations 11.

$$A \cdot e^{i\alpha} + C \cdot e^{i\gamma} =$$
$$\sqrt{A^2 + C^2 + 2AC\cos(\alpha - \gamma)} \cdot e^{iarctg\left[\frac{A \cdot \sin\alpha + C \cdot \sin\gamma}{A \cdot \cos\alpha + C \cdot \cos\gamma}\right]}$$
$$B \cdot e^{i\beta} + C \cdot e^{i\gamma} =$$
$$\sqrt{B^2 + C^2 + 2BC\cos(\beta - \gamma)} \cdot e^{iarctg\left[\frac{B \cdot \sin\beta + C \cdot \sin\gamma}{B \cdot \cos\beta + C \cdot \cos\gamma}\right]}$$

Equations 11

Denoting the topographic phases of the first diffraction orders of the first and second gratings as $\varphi_1$ and $\varphi_2$, respectively, the amplitude and phase of the reference signal may be configured to minimize a difference of topographic phases between zeroth and first order diffraction signals from at least two target layers of target 90. Resulting from Equations 11, the best operating condition may be found by minimizing the expression of Equation 12.

$$\min\left\{\left[\frac{A \cdot \sin\alpha + C \cdot \sin\gamma}{A \cdot \cos\alpha + C \cdot \cos\gamma} - tg(\varphi_1)\right]^2 + \left[\frac{B \cdot \sin\beta + C \cdot \sin\gamma}{B \cdot \cos\beta + C \cdot \cos\gamma} - tg(\varphi_2)\right]^2\right\}$$

Equation 12

Reducing the difference of the topographic phases between first and zero orders for both gratings simultaneously, the best contrast positions of both layers are provided to be close to each other, to allow measuring both layers in the same focus position.

A complementary approach sets dark field imaging metrology as departing point. While bright field imaging uses zeroth and first diffraction order in collection path, dark field imaging blocks the zeroth order and uses only higher diffraction orders, typically the first diffraction orders for image formation, achieving superior precision and accuracy of the overlay measurement. The common limitation of bright and dark field imaging is low diffraction efficiency, namely when amplitudes of the EM waves diffracted by target 90 into the first diffraction orders is very low. The bright field (BF) and dark field (DF) imaging intensities are expressed in Equations 13, with $I_{BF}(x)$ denoting the intensity observed at detector 80, $a_0$, $a_1$ and $a_{-1}$ are respectively the amplitudes of the $0^{th}+1^{st}$ and $-1^{st}$ diffraction orders; $\Psi$ is the mean phase at the pupil plane between the $0^{th}$ and $\pm 1^{st}$ diffraction orders, $\delta a_1$ is the difference in the amplitudes of the positive and negative orders, and $\delta\phi$ is the phase difference.

$$I_{BF}(x) = |a_0|^2 + |a_1|^2 + |a_{-1}|^2 +$$
$$4a_0\overline{a_1}\cos[\Psi]\cos\left[\frac{2\pi(x-x_0)}{P} + \delta\phi + \delta a_1 \tan\Psi\right] +$$
$$a_1 a_{-1}\cos\left[\frac{4\pi(x-x_0)}{P} + 2\delta\phi\right]$$
$$I_{DF}(x) = |a_1|^2 + |a_{-1}|^2 + 2a_1 a_{-1}\cos\left[2\frac{2\pi(x-x_0)}{P} + 2\delta\phi\right]$$

Equations 13

In bright field imaging, it was shown that the phase disturbance introduces an error that is limited by the geometrical ambiguity of the target itself, while the term $\delta a_1 \tan \Psi$ might introduce errors exceeding several nanometers, if measured in improper conditions $$(\Psi \to \pm \frac{\pi}{2},$$

see derivations above). While dark field imaging resolves the inaccuracy problem, it typically suffers significant light starvation as well as the effect of stray light and ghosts of the optical system, as its signal consists solely of high diffraction orders.

In the case of low diffraction efficiency, the precision of the grating position measurement in either type of the imaging can be expressed as in Equations 14, with $\alpha$ and $\beta$ being the noise properties of the light source and the detector, respectively, and $A_0$ and $A_{Signal}$ are the amplitudes of the zeroth modulation frequency and pitch harmonics, respectively. The general expression is approximated for bright field imaging, assuming that the intensity at the zeroth order dominates over the detector noise, and for dark field imaging.

$$\Delta x \propto \frac{PixelSize}{P} \frac{\sqrt{\alpha A_0 + \beta}}{A_{Signal}}$$

$$\Delta x_{BF} \propto \frac{PixelSize}{P} \frac{\sqrt{\alpha a_0^2 + \beta}}{a_0 \overline{a_1}} \approx \frac{PixelSize}{P} \frac{\sqrt{\alpha}}{\overline{a_1}}$$

$$\Delta x_{DF} \propto \frac{PixelSize}{P} \frac{\sqrt{\alpha \overline{a_1}^2 + \beta}}{\overline{a_1}^2} \approx \frac{PixelSize}{P} \frac{\sqrt{\beta}}{\overline{a_1}^2}$$

Equation 14

Therefore, once the diffraction efficiency of the target falls to the level in which the signal is dominated by the detector noise, bright-field measurement is becoming advantageous over dark-field imaging. Nevertheless, total signal is limited by the dynamic range of the detector, such that non-saturation of the camera requires the fulfillment of the condition expressed in Equation 15, with $\Gamma$ denoting the saturation level of the camera (detector).

$$|-a_0|^2 + 4a_0\overline{a_1} < \Gamma$$

Equation 15

Equations 16 express the resulting limitations for the amplitude of the zeroth order EM field pathing the collection pupil, in terms of amplitude and intensity.

$$a_0^2 < a_1^2 \left[\sqrt{\frac{\Gamma}{a_1^2} + 4} - 2\right]^2;$$

$$\frac{I_0}{I_1} < \left(\sqrt{\frac{\Gamma}{I_1} + 4} - 2\right)^2$$

Equation 16

This derivation suggests several implementations: (i) Referring to FIG. 3A, spatial filter 115 may be implemented as a leaky blocker, for example to control the amplitude of the zeroth order using an adjustable ND filter as spatial filter 115 while using narrow illumination NA, to ensure separation between zeroth and higher diffraction orders. As measurement accuracy require particular phase relations between zeroth and first diffraction orders phase control may be implemented by zonal phase plates at collection pupil area 120. (ii) Referring to FIG. 3A, spatial filter 115 may be implemented as an adaptive optical element configured to provide simultaneous phase and amplitude control, e.g., a DLP (digital light processing device, such as an array of individually actuated micro-mirrors, or deformable mirror membrane) providing the phase and amplitude control by surface adjustments (e.g., mirror angles and device topography). (iii) Referring to FIG. 6, attenuator 179 may be variable, and implemented according to the following derivation.

Equations 17 expresses the zeroth order signal as a sum of the signals reflected from target 90 and from mirror 175, with $a_w$ denoting the amplitude of the zeroth order reflected from the wafer (target 90), and $a_r$ denoting the amplitude of the EM field reflected from reference mirror 175; and with $\Psi$ denoting the topographic phase of the zeroth order with respect to first diffraction orders, and $\phi_r$ denoting the phase of the reference EM field at the pupil plane. The effective zeroth order signal is expressed using $a_0'$ and $\Psi_0'$.

$$E_0 = a_w e^{i\Psi} + a_r e^{i\Phi_r} = a_0' e^{i\Psi'};$$

$$a_0' = \sqrt{a_w^2 + a_r^2 + 2a_w a_r \cos(\Psi - \Phi)};$$

$$\Psi' = \tan^{-1}\frac{a_w \sin\Psi + a_r \sin\Phi}{a_w \cos\Psi + a_r \cos\Phi}$$

Equations 17

As a result, using attenuator 179 to control the amplitude $a_r$ and phase $\Phi_r$ of reference arm 178 provides any arbitrary zeroth order field to be collected at detector 80 and according to the principles disclosed above, provides thereby superior accuracy and precision as well as improved contrast and signal intensity in imaging-based overlay (IBO) measurements.

Figure 7:
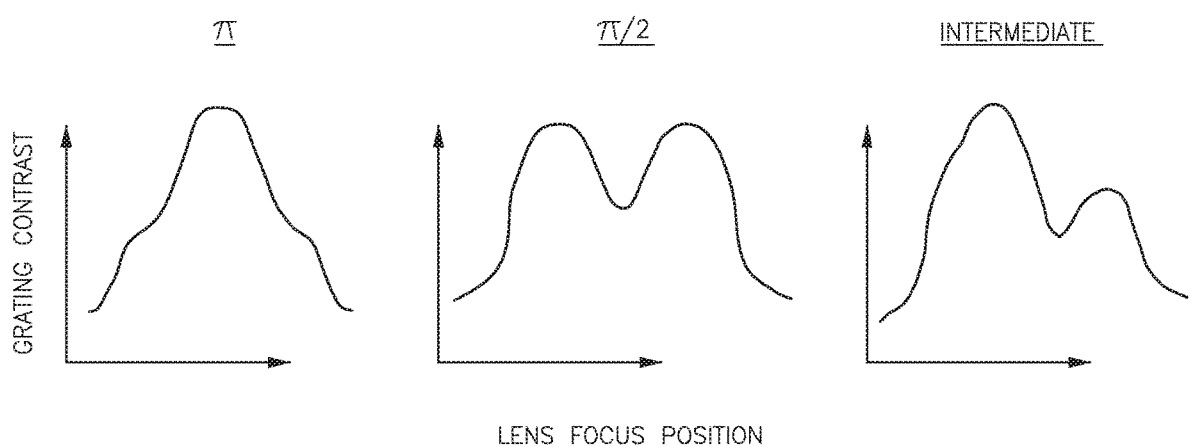
FIG. 7 is a high level schematic illustration of contrast functions as criteria for topographic phase control, according to some embodiments of the invention.

FIG. 7 is a high level schematic illustration of contrast functions as criteria for topographic phase control, according to some embodiments of the invention. Contrast functions which are defined as the grating contrast as a function of the lens focus position, are presented as practical success criterion for topographic phase control in imaging. As shown above (see e.g., Equations 2), any deviation of the focus lens position from the grating position leads to an increase of the phase spread between different illumination angles, resulting in contrast reduction (the larger the deviation the greater the contrast reduction). The best measurement condition in imaging corresponds to a phase difference between zero and first diffraction orders which is integer multiple of π. In this case the grating focus position coincides with best contrast position of the measured signal and there is no spread of topographic phase (induced by defocus) between different pupil illumination points. Under these conditions, the contrast function (marked in FIG. 7 by "π") is a symmetric function with one well distinguished peak. In the opposite, worst measurement condition, the phase difference between the zeroth and first diffraction orders is π/2 and the equivalent contrast is achieved in the contrast reversal position corresponding to the phase difference of π/2. The corresponding behavior of the contrast function has two equal peaks (marked in FIG. 7 by "π/2"). Any intermediate condition provides an asymmetric contrast function (marked in FIG. 7 by "intermediate"). The contrast function may this be used to optimize the imaging measurement conditions.

Metrology tool 85 comprising optical system 110 and calibration module 112 (see FIG. 4A) may be configured to derive, through optical system 110, a contrast function of an imaging target, and adjust measurement conditions of optical system 110 to modify the derived contrast function to have a single peak (as in FIG. 7). Metrology tool 85 may be configured to carry out imaging metrology measurements at the adjusted measurement conditions.

In scatterometry overlay (SCOL) metrology, similar considerations are applicable as presented above for imaging metrology. In particular, similar target design considerations in conjunction with selections of wavelength and polarization are likewise applicable. Moreover, as SCOL signal is measured in the pupil coordinates (angle of incidence multiplexing, at pupil plane 120), post-measurement selection of proper AOI (pupil pixels) is possible to reach the most accurate measurement conditions.

For best sensitivity to overlay and accuracy (robustness to asymmetry and pad-to-pad variations), the preferable phase between fields is $$\pm \frac{\pi}{2},$$

as shown in the following derivation. FIG. 8 is a high level schematic illustration of a scatterometry grating-over-grating target 90, according to some embodiments of the invention. SCOL target 90 comprises at least two cells 90A ("+cell"), 90B ("–cell") with opposite offsets $+f_0$ and $-f_0$, respectively, of top grating 91B with respect to bottom grating 91A (grating pitch is marked by Δ). A cell model 90C is presented for the diffracted electromagnetic (EM) fields, diffracted by upper and lower gratings (91B, U and 91A, L respectively) of a SCOL target cell, at the same diffraction orders (−1, +1). The topographic phase in DBO (diffraction-based overlay metrology) is defined as the mean phase difference between electromagnetic (EM) fields diffracted by the upper and lower gratings. The diffracted orders are approximated in Equations 18. $U_{\pm 1}^+$ and $U_{\pm 1}^-$ denote the total fields scattered by upper grating 91B of first (positive offset) and second (negative offset) cells 90A, 90B, respectively. The sign in superscript indicate cell's offset, the subscript indicates scattering order. $L_{\pm 1}^+$ and $L_{\pm 1}^-$ denote the fields diffracted by lower (process) gratings 91A. $u_{\pm 1}^\pm$ and $l_{\pm 1}^\pm$ denote amplitudes of the fields, $\psi_{\pm 1}^+$ denotes the topographic phase of the field diffracted by upper gratings 91B (cell and order as indicated by corresponding super and sub scripts) and $\phi_{\pm 1}^+$ denotes the total phase (topographic+ Optical Path Difference (OPD) with respect to upper grating 91B) of the fields diffracted by lower grating 91A. $I_{\pm 1}^+$ and $I_{\pm 1}^-$ denote the corresponding signal intensities. The asterisk (*) denotes complex conjugation as an operation and c.c. stands for additional complex conjugated terms.

$$U_{\pm 1}^+ \approx u_{\pm 1}^+ e^{i\left(\pm \frac{2\pi(\Delta + f_0)}{P} + \psi_{\pm 1}^+\right)};$$

$$L_{\pm 1}^+ = l_{\pm 1}^+ e^{i\phi_{\pm 1}^+};$$

$$U_{\pm 1}^- \approx u_{\pm 1}^- e^{i\left(\pm \frac{2\pi(\Delta - f_0)}{P} + \psi_{\pm 1}^-\right)};$$

$$L_{\pm 1}^- = l_{\pm 1}^- e^{i\phi_{\pm 1}^-}$$

$$I_{\pm 1}^+ = |u_{\pm 1}^+|^2 + |l_{\pm 1}^+|^2 + U_{\pm 1}^+ \times L_{\pm 1}^{+*} + c.c.$$

$$= u_{\pm 1}^+ l_{\pm 1}^+ \cos\left(\pm \frac{2\pi(\Delta + f_0)}{P} + \psi_{\pm 1}^+ - \phi_{\pm 1}^+\right)$$

$$I_{\pm 1}^- = |u_{\pm 1}^-|^2 + |l_{\pm 1}^-|^2 + U_{\pm 1}^- \times L_{\pm 1}^{-*} + c.c =$$

$$u_{\pm 1}^+ l_{\pm 1}^+ \cos\left(\pm \frac{2\pi(\Delta + f_0)}{P} + \psi_{\pm 1}^- - \phi_{\pm 1}^-\right)$$

Equations 18

Equations 19 introduce and define four physical variables. In the following derivation constant terms $|u_{\pm 1}^\pm|^2 + |l_{\pm 1}^\pm|^2$ are omitted for simplicity, assuming sufficient similarity between cells and symmetry of the gratings.

$\mathcal{A}^\pm$—Mean interference term amplitude of corresponding cell.

$$\mathcal{A}^\pm = \frac{u_{+1}^\pm l_{+1}^\pm + u_{-1}^\pm l_{-1}^\pm}{2}$$

$\mathcal{B}^\pm$—Asymmetry between amplitudes light scattered to each one of the orders.

$$\mathcal{B}^\pm = \frac{u_{+1}^\pm l_{+1}^\pm - u_{-1}^\pm l_{-1}^\pm}{2}$$

$\alpha^\pm$—Mean Phase difference between EM waves arriving to detector after scattering at upper and lower gratings.

$$\alpha^\pm = \frac{(\psi_{+1}^\pm - \phi_{+1}^\pm) + (\psi_{-1}^\pm - \phi_{-1}^\pm)}{2}$$

$\beta^\pm$—Asymmetry in phase differences of EM waves scattered by gratings into either $+1^{st}$ or $-1^{st}$ orders.

$$\beta^\pm = \frac{(\psi_{+1}^\pm - \phi_{+1}^\pm) - (\psi_{-1}^\pm - \phi_{-1}^\pm)}{2}$$

Equations 19

Using $\mathcal{A}^\pm$, $\mathcal{B}^\pm$, $\alpha^\pm$, $\beta^\pm$, the differential signals for cells 90A, 90B are expressed in Equations 20. The differential signals are expressed in a general form, disregarding terms stemming from multiple re-scattering and depending differently on relative displacements between the gratings, as the relative intensity of these terms depends on high powers of the diffraction efficiency (DE) of the gratings which practically does not exceed several percent.

$$D^{\pm} = I^{\pm}_{+1} - I^{\pm}_{-1} =$$

$$\mathcal{A}^{\pm}\sin\left[\frac{2\pi(\Delta \pm f_0)}{P} + \beta^{\pm}\right]\sin\alpha^{\pm} + \mathcal{B}^{\pm}\cos\left[\frac{2\pi(\Delta \pm f_0)}{P} + \beta^{\pm}\right]\cos\alpha^{\pm} = D^{\pm} =$$

$$\mathcal{A}^{\pm}\sin\alpha^{\pm}\left\{\sin\left[\frac{2\pi(\Delta \pm f_0)}{P} + \beta^{\pm}\right] + \frac{\mathcal{B}^{\pm}}{\mathcal{A}^{\pm}\tan\alpha^{\pm}}\cos\left[\frac{2\pi(\Delta \pm f_0)}{P} + \beta^{\pm}\right]\right\}$$

Alternative Form 1:

$$D^{\pm} = \sqrt{(\mathcal{A}^{\pm}\sin\alpha^{\pm})^2 + (\mathcal{B}^{\pm}\cos\alpha^{\pm})^2} \times$$

$$\sin\left\{\pm\frac{2\pi f_0}{P} + \frac{2\pi}{P}\left[\Delta + \frac{P}{2\pi}\left(\beta^{\pm} + \tan^{-1}\left[\frac{\mathcal{B}^{\pm}}{\mathcal{A}^{\pm}\tan\alpha^{\pm}}\right]\right)\right]\right\}$$

Alternative Form 2:

$$D^{\pm} = \mathcal{A}^{\pm}\sin\alpha^{\pm}\sqrt{1 + \left(\frac{\mathcal{B}^{\pm}}{\mathcal{A}^{\pm}\tan\alpha^{\pm}}\right)^2} \times \qquad \text{Equations 20}$$

$$\sin\left\{\pm\frac{2\pi f_0}{P} + \frac{2\pi}{P}\left[\Delta + \frac{P}{2\pi}\left(\beta^{\pm} + \tan^{-1}\left[\frac{\mathcal{B}^{\pm}}{\mathcal{A}^{\pm}\tan\alpha^{\pm}}\right]\right)\right]\right\}$$

Since the differential signal at each of the cells ($D^{\pm}$) serves as main observable in first order SCOL, Equations 20 provide the basis for sensitivity and error analysis.

The term $$\frac{P}{2\pi}\left(\beta^{\pm} + \tan^{-1}\left[\frac{\mathcal{B}^{\pm}}{\mathcal{A}^{\pm}\tan\alpha^{\pm}}\right]\right)$$

may be measured as an addition to the overlay due to target asymmetry. In a way similar to situation in imaging (see Equation 7), phase asymmetry ($\beta^{\pm}$) manifested as a linear addition to the proper overlay, while the effect of amplitude asymmetry $$\left(\frac{\mathcal{B}^{\pm}}{\mathcal{A}^{\pm}}\right)$$

is amplified by a combination of topographic phases and OPD of the orders scattered by upper and lower gratings $$\left(\frac{1}{\tan\alpha}\right).$$

In the worst possible case of $\to n\pi$ ($\tan\alpha \to 0$), the error introduced by the amplitude asymmetry might reach $$\pm\frac{P}{2}.$$

On the other hand, in optimal situation of $$\alpha \to \pm\frac{\pi}{2};$$

the amplified error vanishes, as $\tan\alpha \to \infty$. It is noted that the topographic phases yielding best and worst results are opposite in scatterometry with respect to imaging, as in SCOL differential signals (difference of the interference terms) are measured whereas in imaging a sum of the interference terms is measured.

Equations 21 estimate the magnitude d of the differential signal and it's first and second derivate.

$$d = (\mathcal{A}\sin\alpha)^2 + (\mathcal{B}\cos\alpha)^2 = \qquad \text{Equations 21}$$

$$\frac{1}{2}(\mathcal{A}^2 + \mathcal{B}^2) - \frac{1}{2}(\mathcal{A}^2 - \mathcal{B}^2)\cos 2\alpha;$$

$$d' = \frac{d}{d\alpha}[(\mathcal{A}\sin\alpha)^2 + (\mathcal{B}\cos\alpha)^2] =$$

$$(\mathcal{A}^2 - \mathcal{B}^2)\sin 2\alpha = 0 \Rightarrow \alpha = \frac{n\pi}{2};$$

$$d'' = \frac{d}{d\alpha}[(\mathcal{A}\sin\alpha)^2 + (\mathcal{B}\cos\alpha)^2] =$$

$$2(\mathcal{A}^2 - \mathcal{B}^2)\cos 2\alpha; \text{ assuming } \mathcal{B} < \mathcal{A}$$

$$\Rightarrow \quad \text{for: } \alpha = 0, \pi \ldots ; d'' > 0 \Rightarrow D \text{ is at minimum;}$$

$$\text{for: } \alpha = \pm\frac{\pi}{2} \ldots ; d'' < 0 \Rightarrow D \text{ is at maximum.}$$

Similarly to situation in imaging, the strongest signal should be obtained at phase relations which are optimal for the measurement. However, it is difficult to decouple the scattering efficiency of the gratings from the relative phase between the EM fields diffracted by upper and lower gratings 91B, 91A. Since neither $\mathcal{A}$ nor $\mathcal{B}$ are known a priori, and since nothing is known about $\alpha$; no clear behavior of a measurable quantity (e.g., the magnitude of $D^{\pm}$ with $\alpha$) can be formulated.

Currently SCOL algorithms calculate the signal at each pixel using the expression $$S = \frac{D^+ + D^-}{D^+ - D^-}.$$

Two assumptions are customarily made, that the gratings are symmetric and the illumination is nearly normal and that target cells 90A, 90B are identical except for the offset. The model implications of these assumptions are expressed in Equations 22.

$$u^{\pm}_{+1} = u^{\pm}_{-1} \wedge l^{\pm}_{+1} = l^{\pm}_{-1} \Rightarrow \mathcal{B}^{\pm} = 0 \qquad \text{Equations 22}$$

$$\psi^{\pm}_{+1} = \psi^{\pm}_{-1} \wedge \phi^{\pm}_{+1} = \phi^{\pm}_{-1} \Rightarrow \beta^{\pm} = 0$$

$$D^{\pm} = I^{\pm}_{+1} - I^{\pm}_{-1} = \mathcal{A}^{\pm}\sin\left[\frac{2\pi(\Delta \pm f_0)}{P}\right]\sin\alpha^{\pm}$$

$$\mathcal{A}^+ = \mathcal{A}^- \equiv \mathcal{A}; \alpha^+ = \alpha^- \equiv \alpha$$

$$D^{\pm} = I^{\pm}_{+1} - I^{\pm}_{-1} = \mathcal{A}\sin\left[\frac{2\pi(\Delta \pm f_0)}{P}\right]\sin\alpha$$

$$S = \frac{D^+ + D^-}{D^+ - D^-} = \tan\left(\frac{2\pi\Delta}{P}\right)\cot\left(\frac{2\pi f_0}{P}\right)$$

However, in case the gratings have the same shape but their optical thickness differs. Equations 23 express the model implications.

$$u^{\pm}_{+1} = u^{\pm}_{-1} \wedge l^{\pm}_{+1} = l^{\pm}_{-1} \Rightarrow \mathcal{B}^{\pm} = 0; \Rightarrow \mathcal{A}^{+} = \mathcal{A}^{-} \equiv \mathcal{A};$$ Equations 23

$$\psi^{\pm}_{+1} = \psi^{\pm}_{-1} \neq \psi^{-}_{+1} = \psi^{-}_{-1}; \phi^{\pm}_{+1} =$$

$$\phi^{\pm}_{-1} \neq \phi^{-}_{+1} = \phi^{-}_{-1}; \Rightarrow \beta^{\pm} = 0; \alpha^{+} \neq \alpha^{-};$$

$$D^{\pm} = I^{\pm}_{+1} - I^{\pm}_{-1} = \mathcal{A}^{\pm} \sin\left[\frac{2\pi(\Delta \pm f_0)}{P}\right] \sin\alpha^{\pm}$$

$$S = \frac{D^{+} + D^{-}}{D^{+} - D^{-}} = \frac{\sin\left[\frac{2\pi(\Delta + f_0)}{P}\right]\sin\alpha^{+} + \sin\left[\frac{2\pi(\Delta - f_0)}{P}\right]\sin\alpha^{-}}{\sin\left[\frac{2\pi(\Delta + f_0)}{P}\right]\sin\alpha^{+} - \sin\left[\frac{2\pi(\Delta - f_0)}{P}\right]\sin\alpha^{-}}$$

$$\sin\left[\frac{2\pi(\Delta \pm f_0)}{P}\right] = \sin\left[\frac{2\pi}{P}\Delta\right]\cos\left[\frac{2\pi}{P}f_0\right] \pm \cos\left[\frac{2\pi}{P}\Delta\right]\sin\left[\frac{2\pi}{P}f_0\right] \Rightarrow$$

$$S = \frac{D^{+} + D^{-}}{D^{+} - D^{-}} = \frac{\sin\left[\frac{2\pi}{P}\Delta\right]\cos\left[\frac{2\pi}{P}f_0\right]\{\sin\alpha^{+} + \sin\alpha^{-}\} + \cos\left[\frac{2\pi}{P}\Delta\right]\sin\left[\frac{2\pi}{P}f_0\right]\{\sin\alpha^{+} - \sin\alpha^{-}\}}{\sin\left[\frac{2\pi}{P}\Delta\right]\cos\left[\frac{2\pi}{P}f_0\right]\{\sin\alpha^{+} - \sin\alpha^{-}\} + \cos\left[\frac{2\pi}{P}\Delta\right]\sin\left[\frac{2\pi}{P}f_0\right]\{\sin\alpha^{+} + \sin\alpha^{-}\}}$$

Using the notation $$\alpha = \frac{\alpha^{+} + \alpha^{-}}{2}; \gamma = \frac{\alpha^{+} - \alpha^{-}}{2} \Rightarrow \alpha^{\pm} = \alpha \pm \gamma;$$

and remembering the physical meaning of the parameters: Δ being the overlay between two gratings, $f_0$ being the intentional offset between the two cells, α being the phase (including OPD) between orders scattered by upper and lower gratings to the same diffraction order, and γ being mainly the OPD difference between cells (due to the additional assumptions), the signal may be further derived as expressed in Equation 24, resulting in the following simplified expression $$S = \frac{D^{+} + D^{-}}{D^{+} - D^{-}}$$ Equation 24

$$= \frac{\sin\left[\frac{2\pi}{P}\Delta\right]\cos\left[\frac{2\pi}{P}f_0\right]\sin\alpha\cos\gamma + \cos\left[\frac{2\pi}{P}\Delta\right]\sin\left[\frac{2\pi}{P}f_0\right]\cos\alpha\sin\gamma}{\sin\left[\frac{2\pi}{P}\Delta\right]\cos\left[\frac{2\pi}{P}f_0\right]\cos\alpha\sin\gamma + \cos\left[\frac{2\pi}{P}\Delta\right]\sin\left[\frac{2\pi}{P}f_0\right]\sin\alpha\cos\gamma}$$

-continued $$= \frac{\tan\left[\frac{2\pi}{P}\Delta\right]\tan\alpha + \tan\left[\frac{2\pi}{P}f_0\right]\tan\gamma}{\tan\left[\frac{2\pi}{P}\Delta\right]\tan\gamma + \tan\left[\frac{2\pi}{P}f_0\right]\tan\alpha}$$

The implication of assuming different optical thickness between the gratings results in tan γ≠0, returning otherwise to Equations 22. While in case |tan α|≫|tan γ| a similar approximation holds (e.g., when $\tan\alpha \to \pm\infty$ as $\alpha \to \pm\frac{\pi}{2}$), such approximation for nearly any $$\gamma \neq \pm\frac{\pi}{2}$$

clearly results in neglecting the wrong terms from the standard model. Moreover, if tan α→0 (termed resonance conditions below), the measured signal for any γ, with tan γ≠0, behaves exactly as $S^{-1}$ of the expected signal S.

The consequence is that reducing optical thickness (pad-to-pad) sensitivity and grating asymmetry amplification effects (see discussion above for Equations 20) may be achieved by finding conditions for which $$\alpha \cong \pm\frac{\pi}{2}.$$

However, the aspired conditions of $$\alpha = \pm\frac{\pi}{2}$$

show no special features, neither in pupil image nor in the differential signal, in contrast to unwanted conditions of α=±nπ which yield constructive or destructive interference between orders from the upper and lower gratings, and are often indicated by clear fringes (either bright or dark) at pupil images and drastically reduced sensitivity to overlay (dark fringe in differential signal).

Figure 9:
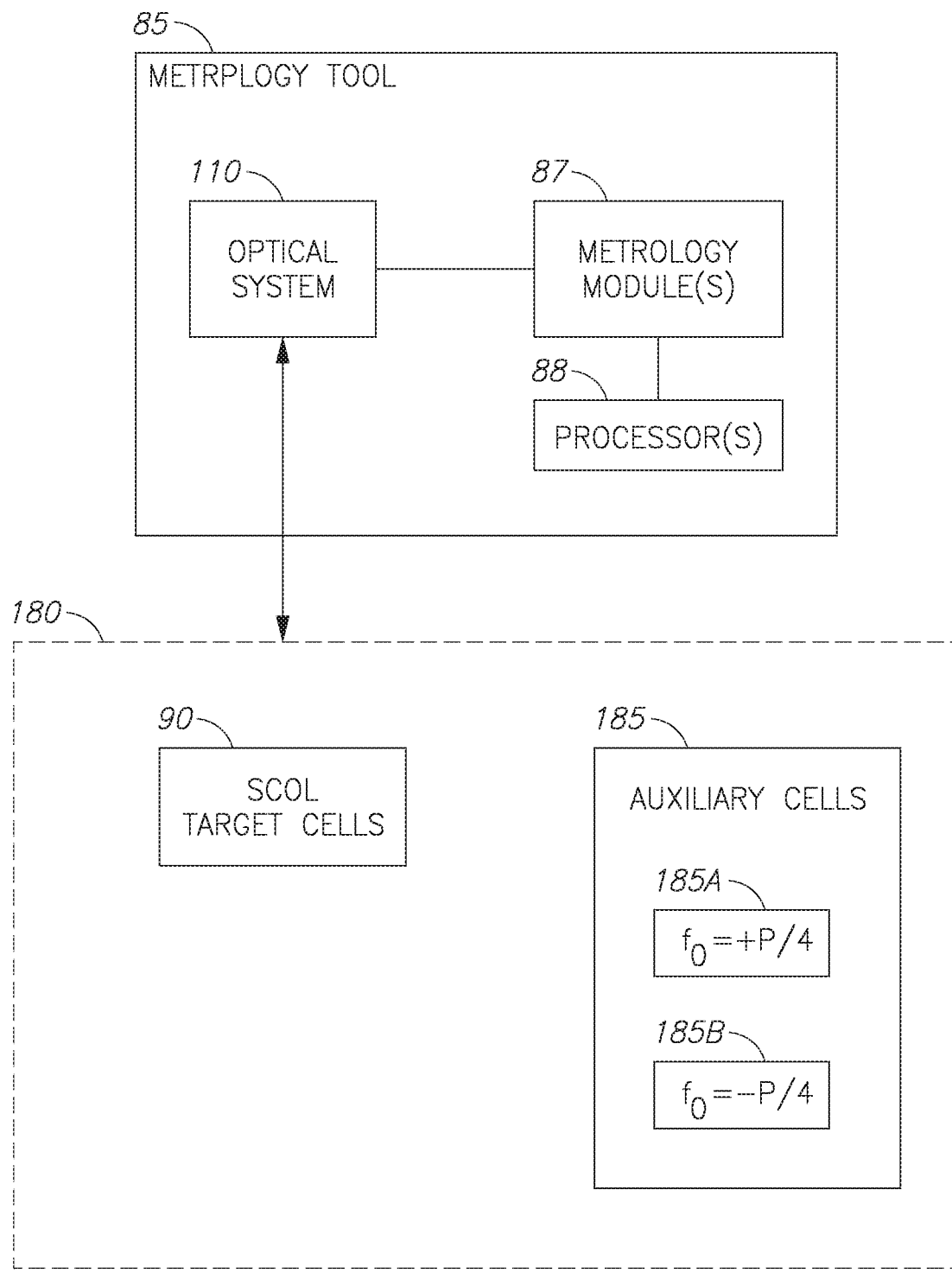
FIG. 9 is a high level schematic illustration of a SCOL target with auxiliary cells, measured by a metrology tool, according to some embodiments of the invention.

FIG. 9 is a high level schematic illustration of a SCOL target 180 with auxiliary cells 185, measured by metrology tool 85, according to some embodiments of the invention. Metrology tool 85 comprises optical system 110 as well as metrology module(s) 87 associated with one or more processor(s) 88—applicable to any of the disclosed embodiments, possibly with the disclosed configurations of optical system(s) 110 and metrology module(s) 87. Metrology target 90 may comprise at least two cells, each having at least two target layers with periodic structures having a pitch p and shifted with respect to each other by an opposite offsets in the at least two cells. At least two auxiliary, specially designed measurement cells 185 may be introduced in target 180 in addition to SCOL target cells 90 to determine the topographic phase on a pixel-wise basis. For example, two auxiliary cells 185A, 185B having intentional offsets of a quarter pitch $$\pm \frac{P}{4},$$

respectively may be introduced, so that auxiliary cells have the periodic structures of target 90 shifted by ±p/4 with respect to each other, at the respective auxiliary cells. Pupil images of auxiliary cells 185 may be used to perform the calculation of W expressed in Equation 25, with α representing the topographic phase, $$I_{+1}^{\frac{1}{4}} \text{ and } I_{-1}^{\frac{1}{4}}$$

denoting the intensities of the pupil images measured for the first and minus first orders (as indicated by subscripts) of auxiliary cell 185A with offset of $$\frac{P}{4}$$

in the positive overlay direction.

$$I_{+1}^{-\frac{1}{4}} \text{ and } I_{-1}^{-\frac{1}{4}},$$

denote the respective intensities for auxiliary cell 185B with offset $$\frac{P}{4}$$

in the negative overlay direction, $I_{+1}^{0}$ and $I_{-1}^{0}$ denote the respective intensities for standard SCOL cell(s) 90 with no special displacement (i.e., with standard designed offsets with standard $\pm f_0$).

$$W = \frac{\left(I_{+1}^{\frac{1}{4}} + I_{-1}^{\frac{1}{4}}\right) - \left(I_{+1}^{-\frac{1}{4}} + I_{-1}^{-\frac{1}{4}}\right)}{\left(I_{+1}^{0} - I_{-1}^{0}\right)} = \frac{\cos\alpha}{\sin\alpha} \cong \cot\alpha \quad \text{Equation 25}$$

It is noted that $$\alpha = \pm \frac{\pi}{2}$$

in pixels for which W=0. Therefore, selecting pixels or regions of detector 80 (corresponding to illumination angle θ) and/or wavelengths λ corresponding to small values of W (e.g., W≅0) provide significant improvement of accuracy by suppressing the target's sensitivity to layers' thickness variations between adjacent cells, as well as the effect of grating asymmetries.

FIG. 10 is a high level flowchart illustrating a method 200, according to some embodiments of the invention. The method stages may be carried out with respect to the systems and tools described above, which may optionally be configured to implement method 200. Method 200 may be at least partially implemented by at least one computer processor, e.g., in a metrology module. Certain embodiments comprise computer program products comprising a computer readable storage medium having computer readable program embodied therewith and configured to carry out of the relevant stages of method 200. Certain embodiments comprise target design files of respective targets designed by embodiments of method 200.

These method stages are described in more detail with respect to the systems and tools described above and optionally configured to implement method 200. Method stages of different aspects of the invention may be combined according to specified requirements.

Method 200 may comprise deriving, in an optical system of an imaging metrology tool, a dependency of an overlay error magnification error on a level of defocusing (stage 210), and operating the optical system at a narrow spectral range, Δλ≤10 nm, at a narrow illumination numerical aperture, NA≤0.1, and at a focus position that corresponds to zero overlay error magnification according to the derived dependency (stage 220).

Method 200 may comprise grabbing a plurality of metrology target images at a corresponding plurality of focus positions (stage 230), estimating an inaccuracy magnification factor of the grabbed images (stage 250), determining a best contrast position by identifying a sign change of the inaccuracy magnification factor with respect to the focus positions (stage 260), and operating the metrology tool at the determined best contrast position (stage 270). Grabbing 230 may be is carried out simultaneously (stage 240) and simultaneous grabbing 240 may be carried out by positioning at least two beam splitting elements along a collection path of the metrology tool (stage 242) to provide the plurality of focus positions having different collection path lengths (stage 244). In certain embodiments, method 200 further comprises using a reticle at a field plane of the metrology tool, configured as a reference for target images at the focus locations (stage 246).

Method 200 may comprise deriving a dependency of a topographic phase of an imaging metrology target on a measurement wavelength (stage 280), adjusting the measurement wavelength to make the topographic phase an integer multiple of π (stage 290), e.g., in a range of ±10 nm, and carrying out imaging metrology measurements of the imaging metrology target at the adjusted measurement wavelength (stage 300).

Method 200 may comprise integrating, in a collection path of an imaging metrology optical system, an adjustable reference path comprising a reference signal (stage 320), and adjusting a phase of the reference signal to modify a topographic phase of an imaging metrology target to be an integer multiple of π (330). The adjustable reference path may be configured in the optical system as a Linnik interferometer with a reference objective identical to an objective of the imaging metrology optical system and an adjustable mirror (stage 322). Method 200 may comprise minimizing a difference of topographic phases between zeroth and first order diffraction signals from at least two target layers (stage 332), e.g., according to Equation 12.

Method 200 may comprise adding to a scatterometry target at least two auxiliary cells having periodic structures with a same pitch p as periodic structures in the scatterometry target, shifted by ±p/4 with respect to each other (stage 340), and measuring a topographic phase of the scatterometry target by measuring diffraction signals from the at least two auxiliary cells according to Equation 25 (stage 350).

Method 200 may comprise deriving a contrast function of an imaging target (stage 360), adjusting measurement conditions to modify the derived contrast function to have a single peak (stage 370), and carrying out imaging metrology measurement at the adjusted measurement conditions (stage 375).

Method 200 may comprise carrying out high topography stack measurements (stage 380) by selecting the collection and illumination numerical apertures (NA's) to have a sum smaller than 2λ/P (stage 382), possibly minimizing the illumination NA to increase the depth of field (DOF) (stage 384); and/or integrating multiple images over multiple focal positions to average out non-symmetric contributions (stage 386).

Any of the data processing stages of method 200 may be carried out by at least one computer processor (stage 390), such as processor(s) 88.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:
1. An imaging metrology tool comprising:
   a calibration module operated by one or more processors configured to derive a dependency of an overlay error magnification on a level of defocusing, wherein the dependency is based on target pitch, target asymmetry, amplitude of a first diffraction order, topographic phase, and defocus, and wherein the amplitude of the first diffraction order is based on amplitudes from a plurality of symmetric rectangular areas, the target pitch, and a phase difference,
   controlling the overlay error magnification, using the calibration module, by adjusting a focus position to reduce a factor that is defined by $\tan(\psi^{(1)}-\psi^{(0)}-2\pi(1-\cos\theta_1)\Delta z/\lambda)$, wherein $\Delta z$ is the level of defocusing, $\lambda$ is an illumination wavelength, $\theta_1$ is an illumination angle of the first diffraction order, and $\psi^{(1)}$ and $\psi^{(0)}$ are topographic phases of the first and the zeroth diffraction orders, respectively, and
   an optical system configured to operate at a narrow spectral range, $\Delta\lambda \leq 10$ nm, at a narrow illumination numerical aperture, $NA \leq 0.1$, and at the focus position that corresponds to zero overlay error magnification according to the derived dependency.
2. The imaging metrology tool of claim 1, wherein the optical system includes an optical assembly comprising beam splitters followed by a mirror configured to provide three respective focal locations approximately at a detection plane.

3. The imaging metrology tool of claim 1, wherein the optical system includes a reticle at a field stop, optics, and beam splitters configured to provide three respective focal locations.

4. The imaging metrology tool of claim 2, wherein the imaging metrology tool includes two of the beam splitters.

5. The imaging metrology tool of claim 2, wherein the optical system provides three images having equal power and corresponding to the three respective focal locations.

6. The imaging metrology tool of claim 5, wherein the three images are detected by a detector.

7. The imaging metrology tool of claim 3, further comprising three detectors, wherein each of the three detectors detects one of the three respective focal locations.

* * * * *